(12) United States Patent
Lok et al.

(10) Patent No.: US 6,709,659 B1
(45) Date of Patent: Mar. 23, 2004

(54) ANTIBODIES THAT BIND TESTIS-SPECIFIC INSULIN HOMOLOG POLYPEPTIDES

(75) Inventors: Si Lok, Seattle, WA (US); Darrell C. Conklin, Seattle, WA (US); Catherine E. Lofton-Day, Brier, WA (US); Stephen R. Jaspers, Edmonds, WA (US); Michael R. Stamm, Everett, WA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

(21) Appl. No.: 09/617,389

(22) Filed: Jul. 17, 2000

Related U.S. Application Data

(63) Continuation-in-part of application No. 09/339,149, filed on Jun. 24, 1999, now abandoned, which is a continuation-in-part of application No. 08/905,267, filed on Aug. 1, 1997, now Pat. No. 5,959,075.

(60) Provisional application No. 60/023,213, filed on Aug. 2, 1996, and provisional application No. 60/031,592, filed on Nov. 21, 1996.

(51) Int. Cl.[7] .................................................. A61K 39/00
(52) U.S. Cl. .................... 424/198.1; 424/184.1; 424/185.1; 530/387.1; 530/387.9; 530/388.24; 530/389.2
(58) Field of Search .................. 424/184.1, 185.1, 424/198.1; 530/387.1, 387.9, 388.24, 389.2

(56) References Cited

FOREIGN PATENT DOCUMENTS

| EP | 351 045 A2 | 1/1990 |
|---|---|---|
| WO | 93/11247 | 6/1993 |
| WO | 95/00645 | 1/1995 |
| WO | 97/16549 | 5/1997 |

OTHER PUBLICATIONS

Bagnell et al., *Journal of Reproduction and Fertility Supplement 48*: 127–138, 1993.
Zhu et al., *Proc. Natl. Acad. Sci. U.S.A. 94*: 4704–4709, 1997.
Juang et al., *Animal Reproduction Science 20*: 21–29, 1989.
Pusch et al., *Endicrinology 137*: 3009–3013, 1996.
Gunnerson et al., *Molecular and Cellular Endicrinology 110*: 55–64, 1995.
Park et al., *Am. J. Obstet. Gynecol. 158*: 974–979, 1988.
Lessing et al., *Journal of Reproductive Medicine 31*: 304–309, 1986.
Juang et al., *Animal Reproduction Science 22*: 47–53, 1990.
Carrell et al., *Endocrine Research 21*: 697–707, 1995.
Lessing et al., *Fertility and Sterility 44*:406–409, 1985.
Colon et al., *Fertility and Sterility 46*: 1133–1139, 1986.
Chassin et al., *Genomics 29*: 465–470, 1995.
TIGR Tentative Consensus Sequence, 1997, THC_T19007.
Lok et al., *Biology of Reproduction 62*: 1593–1599, 2000.
Guellaen, INSERM, 1994, GenBank Acc# T19007.

*Primary Examiner*—Patrick J. Nolan
(74) *Attorney, Agent, or Firm*—Shelby J. Walker

(57) ABSTRACT

The present invention provides testis-specific insulin homolog polypeptides and polynucleotides encoding the polypeptides, as well as related compositions and methods are disclosed. The polypeptides and polynucleotides may be used within methods for enhancing viability of cryopreserved sperm, for enhancing sperm motility, to enhance fertilization in methods of assisted reproduction, as contraceptives and other related uses.

19 Claims, 2 Drawing Sheets

```
            +...110..+....120..+....130..+....140..+....150..+....160..+....170..+....180
IGF2_HUMAN  FPRYPVGKFFQYDTWKQSTQRLRRGLPALLRARRGHVLAKELEAFREAKRHRPLIALPTQDPAHGGAPPEMASNRK
INS_HUMAN   +....110..+....120..+....130..+....140..+....150..+....160..+....170..+....180
REL2_HUMAN  +....110..+....120..+....130..+....140..+....150..+....160..+....170..+....180
REL1_HUMAN  +....110..+....120..+....130..+....140..+....150..+....160..+....170..+....180
HSLILH      +....110..+....120..+....130..+....140..+....150..+....160..+....170..+....180
INSL4       +....110..+....120..+....130..+....140..+....150..+....160..+....170..+....180
zins2_rat   +....110..+....120..+....130..+....140..+....150..+....160..+....170..+....180
zins2_human Y
```

FIGURE 1B

ANTIBODIES THAT BIND TESTIS-SPECIFIC INSULIN HOMOLOG POLYPEPTIDES

REFERENCE TO RELATED APPLICATIONS

This application is a continuation-in-part of U.S. patent application Ser. No. 09/339,149, now abandoned, filed on Jun. 24, 1999, which was a continuation-in-part of U.S. patent application Ser. No. 08/905,267, filed on Aug. 1, 1997, now issued as U.S. Pat. No. 5,959,075, which is related to U.S. Provisional Applications No. 60/023,213, filed on Aug. 2, 1996 and No. 60/031,592, filed on Nov. 21, 1996; and under 35 U.S.C. §119, claims benefit of said Applications, all of which are incorporated herein by reference.

BACKGROUND OF THE INVENTION

Proliferation and differentiation of cells within multicellular organisms is controlled by hormones and polypeptide growth factors. These diffusable molecules allow cells to communicate with each other and act in concert to form organs, and to repair and regenerate damaged tissue. Examples of hormones and growth factors include the steroid hormones (e.g., estrogen, testosterone), parathyroid hormone, follicle stimulating hormone, the interleukins, platelet derived growth factor (PDGP), epidermal growth factor (EGF), granulocyte-macrophage colony stimulating factor (GM-CSF), erythropoietin (EPO), insulin and calcitonin.

Hormones and growth factors influence cellular metabolism by binding to receptors. Receptors may be integral membrane proteins that are linked to signaling pathways within the cell, such as second messenger systems. Other classes of receptors are soluble molecules, such as certain transcription factors.

Insulin belongs to a group of protein/polypeptide hormones. Insulin increases the rate of synthesis of glycogen, fatty acids, and proteins and stimulates glycolysis. It also promotes the transport of glucose, some other sugars, and amino acids into muscle and fat cells. The mature form of insulin consists of a 30 amino acid residue B chain, that is at the N-terminus of the propeptide form, and a 21 amino acid residue A chain, that is C-terminal. Proinsulin also contains a connecting peptide, C-peptide, between the B chain and A chain that is cleaved out to form mature insulin. The B chain and A chain are covalently joined by two disulfide bonds. The B-chain, C-peptide, A-chain motif is found in several other proteins including, relaxin (U.S. Pat. No. 4,835,251, incorporated herein by reference), insulin-like growth factors (IGF) I and II (Bang and Hall, In "Insulin-like Growth Factors", P. N. Schofield (eds.), 151–177, Oxford Univ. Press, Oxford; incorporated herein by reference), Leydig factor (Bullesbach et al., *J. Biol. Chem.* 270:16011–16015, 1995; incorporated herein by reference), and early placenta insulin-like factor (EPIL; Chassin et al., *Genomics* 29:465–470, 1995, incorporated herein by reference). Unlike the other members of the insulin superfamily, IGF I and IGF II have D and E domains that are cleaved post-translationally. Cysteines that are involved in disulfide bonds are conserved in all the members of the family and play a role in the tertiary structure of the molecules.

Spermatogenesis is the process by which a germ cell proceeds through multiple stages of differentiation, and culminates in the formation of a terminally differentiated cell with a unique function. Hematopoiesis can be used as a paradigm for understanding spermatogenesis, and while there are striking parallels between what is known about hematopoiesis and spermatogenesis, the maturation of spermatogonia (germ cells) is less clearly understood than the maturation of hematopoietic stem cells. Particularly deficient is an understanding of factors that regulate the maturation process in spermatogenesis. Recent evidence suggests that some cytokines involved in the progression of stem cells of the hematopoietic lineage to fully differentiated cells are also involved in sperm cell maturation. In a fashion similar to cytokine action in hematopoiesis, these cytokines are thought to act at specific stages in the germ cell's maturation. For example, stem cell factor (also known as Steel factor and c-kit ligand) mRNA is expressed in spermatogonia (Manova et al., *Development* 110:1057–1066, 1990), and administration of a monoclonal antibody to stem cell factor to adult or prepubertal mice causes depletion of differentiating spermatogonia but has no effect on the non-differentiating spermatogonia, or spermatocytes (Yoshinaga et al., *Development* 113:689–699, 1991). Other cytokines that have been associated with spermatogenesis include IL-1, IL-6 and β-TGF (Sharp, Regulation of Spermatogenesis, in Knobil and Neil (ed.), *Physiol. Reproduction*, (2nd ed.), Raven, N.Y., 1994).

Because growth factors have had an enormous impact on our understanding of and ability to treat metabolic and cellular disorders, discovery of new factors is important. A new growth factor found in testis is particularly important for elucidating the spermatogenic process and potentially affecting the outcome of that process.

SUMMARY OF THE INVENTION

The present invention provides an isolated testis-specific insulin homolog polypeptide selected from the group consisting of: (a) polypeptides comprising a sequence of amino acids encoded by the nucleotide sequence as shown in SEQ ID NO: 1; (b) allelic variants of (a); and (c) testis-specific insulin homolog polypeptides which are at least 85% identical to (a) or (b).

In another aspect, the present provides an isolated polynucleotide molecule selected from the group consisting of: (a) DNA molecules encoding a testis-specific insulin homolog polypeptide and comprising a nucleotide sequence as shown in SEQ ID NO: 1 from nucleotide 1 to nucleotide 564; (b) allelic variants of (a); (c) DNA molecules encoding a testis-specific insulin homolog polypeptide which are least 85% identical in nucleotide sequence to (a) or (b); and (e) degenerate nucleotide sequences encoding a testis-specific insulin homolog polypeptide.

In another aspect, the present invention provides an expression vector comprising the following operably linked elements: a transcriptional promoter; a DNA segment selected from the group consisting of: (a) DNA molecules encoding a testis-specific insulin homolog polypeptide and comprising a nucleotide sequence as shown in SEQ ID NO: 1 from nucleotide 1 to nucleotide 564; (b) allelic variants of (a); (c) DNA molecules encoding a testis-specific insulin homolog polypeptide and which are least 85% identical in nucleotide sequence to (a) or (b); and a transcriptional terminator.

In another aspect, the present invention provides a cultured cell into which has been introduced an expression vector comprising the following operably linked elements: a transcriptional promoter; a DNA segment selected from the group consisting of: (a) DNA molecules encoding a testis-specific insulin homolog polypeptide and comprising a nucleotide sequence as shown in SEQ ID NO: 1 from nucleotide 1 to nucleotide 564; (b) allelic variants of (a); (c) DNA molecules encoding a testis-specific insulin homolog polypeptide which are least 85% identical in nucleotide sequence to (a) or (b); and a transcriptional terminator, and wherein the cell expresses a testis-specific insulin homolog polypeptide encoded by the DNA segment.

In another aspect, the present invention provides a method for producing a testis-specific insulin homolog polypeptide comprising culturing a cell into which has been introduced a first expression vector comprising the following operably linked elements: a transcriptional promoter; a DNA segment selected from the group consisting of: (a) DNA molecules encoding a testis-specific insulin homolog polypeptide and comprising a nucleotide sequence as shown in SEQ ID NO: 1 from nucleotide 1 to nucleotide 564; (b) allelic variants of (a); (c) DNA molecules encoding a testis-specific insulin homolog polypeptide which are least 85% identical in nucleotide sequence to (a) or (b); and a transcriptional terminator, whereby the cell expresses a testis-specific insulin homolog polypeptide encoded by the DNA segment, and recovering the testis-specific insulin homolog. Within one embodiment is provided a method for producing a Zins2 testis-specific insulin homolog polypeptide wherein the cell further comprises a second expression vector comprising the following operably linked elements: a transcriptional promoter; a DNA sequence encoding a prohormone convertase; and a transcriptional terminator. Within a related embodiment the prohormone convertase is selected from the group consisting of prohormone convertase 2, prohormone convertase 3, prohormone convertase 4 and furin.

Within another aspect, the invention provides an isolated, mature rat Zins2 testis-specific insulin homolog protein having: a B chain comprising amino acid residue 22 to amino acid residue 52 of SEQ ID NO:2; an A chain comprising amino acid residue 162 to amino acid residue 188 of SEQ ID NO:2; wherein the B chain and A chain are joined by inter- and intra-chain disulfide bonds. Within a related embodiment is provided an isolated, mature rat Zins2 testis-specific insulin homolog protein having: a B chain having the amino acid sequence from amino acid residue 23 to amino acid residue 51 of SEQ ID NO:2; an A chain having the amino acid sequence from amino acid residue 163 to amino acid residue 188 of SEQ ID NO:2, wherein the B chain and A chain are joined by inter- and intra-chain disulfide bonds.

The invention also provides an isolated, mature human Zins2 testis-specific insulin homolog protein having: a B chain comprising amino acid residue 20 to amino acid residue 54 of SEQ ID NO:13; an A chain comprising amino acid residue 172 to amino acid residue 213 of SEQ ID NO:13; wherein the B chain and A chain are joined by inter- and intra-chain disulfide bonds. Within a related embodiment is provided an isolated, mature human Zins2 testis-specific insulin homolog protein having: a B chain having the amino acid sequence from amino acid residue 21 to amino acid residue 53 of SEQ ID NO:13; an A chain having the amino acid sequence from amino acid residue 173 to amino acid residue 198 of SEQ ID NO:13, wherein the B chain and A chain are joined by inter- and intra-chain disulfide bonds.

Within another aspect, the invention provides a post-translationally modified Zins2 testis-specific insulin homolog polypeptide or polypeptide fragment having the amino acid sequence from amino acid residue 53 to amino acid residue 162 of SEQ ID NO:2; the amino acid sequence from amino acid residue 55 to amino acid residue 172 of SEQ ID NO:13 or the amino acid sequence from amino acid residue 201 to amino acid residue 213 of SEQ ID NO:13.

The invention also provides a pharmaceutical composition comprising an isolated testis-specific insulin homolog polypeptide as described above in combination with a pharmaceutically acceptable vehicle.

Also provided by the invention is an antibody that specifically binds to an epitope of an isolated testis-specific insulin homolog polypeptide as described above.

The invention further provides a binding protein that specifically binds to an epitope of an isolated testis-specific insulin homolog polypeptide as described above.

The invention additionally provides a binding protein that specifically binds to an epitope of a polypeptide selected from the group consisting of: (a) polypeptides comprising a sequence of amino acids encoded by the nucleotide sequence as shown in SEQ ID NO:12; (b) allelic variants of (a); and (c) testis-specific insulin homolog polypeptides which are at least 85% identical to (a) or (b).

Within another aspect, the invention provides a method of enhancing viability of cryopreserved sperm for use in fertilization of an egg, wherein a Zins2 testis-specific insulin homolog polypeptide selected from the group consisting of: (a) polypeptides comprising a sequence of amino acids encoded by the nucleotide sequence as shown in SEQ ID NO: 1 or SEQ ID NO:12; (b) allelic variants of (a); and (c) Zins2 testis-specific insulin homolog polypeptides which are at least 85% identical to (a) or (b); is added to sperm, an egg, an egg-sperm mixture, prior to fertilization.

Within another aspect, the invention provides a method of enhancing sperm motility wherein a Zins2 testis-specific insulin homolog polypeptide selected from the group consisting of: (a) polypeptides comprising a sequence of amino acids encoded by the nucleotide sequence as shown in SEQ ID NO: 1 or SEQ ID NO:12; (b) allelic variants of (a); and (c) Zins2 testis-specific insulin homolog polypeptides which are at least 85% identical to (a) or (b); is added to sperm, an egg, an egg-sperm mixture, prior to fertilization. Within a related embodiment is provided a method of enhancing sperm motility wherein the Zins2 testis-specific insulin homolog is added to sperm following cryopreservation.

Within another aspect, the invention provides a method of enhancing an egg-sperm interaction wherein a Zins2 testis-specific insulin homolog polypeptide selected from the group consisting of: (a) polypeptides comprising a sequence of amino acids encoded by the nucleotide sequence as shown in SEQ ID NO: 1 or SEQ ID NO:12; (b) allelic variants of (a); and (c) Zins2 testis-specific insulin homolog polypeptides which are at least 85% identical to (a) or (b); is added to sperm, an egg, an egg-sperm mixture prior to fertilization.

Within anther aspect, the invention provides a method of enhancing fertilization during assisted reproduction wherein a Zins2 testis-specific insulin homolog polypeptide selected from the group consisting of: (a) polypeptides comprising a sequence of amino acids encoded by the nucleotide sequence as shown in SEQ ID NO: 1 or SEQ ID NO:12; (b) allelic variants of (a); and (c) Zins2 testis-specific insulin homolog polypeptides which are at least 85% identical to (a) or (b); is combined with sperm, an egg, an egg-sperm mixture prior to fertilization of the egg. Within one embodiment is provided a method of enhancing fertilization wherein the assisted reproduction is artificial insemination. Within a related embodiment is provided a method of enhancing fertilization wherein the assisted reproduction is in vitro fertilization.

Also provided by the invention is a method of contraception wherein an antagonist of a Zins2 testis-specific insulin homolog polypeptide selected from the group consisting of: (a) polypeptides comprising a sequence of amino acids encoded by the nucleotide sequence as shown in SEQ ID NO: 1 or SEQ ID NO:12; (b) allelic variants of (a); and (c) Zins2 testis-specific insulin homolog polypeptides which are at least 85% identical to (a) or (b); is administered to a recipient to prevent fertilization of an egg. Within a related embodiment is provided a method of contraception according wherein the antagonist is an anti-Zins2 binding protein.

The invention further provides a method of immunocontraception wherein a vaccine containing a Zins2 testis-specific insulin homolog polypeptide selected from the group consisting of: (a) polypeptides comprising a sequence of amino acids encoded by the nucleotide sequence as shown in SEQ ID NO: 1 or SEQ ID NO:12; (b) allelic variants of (a); and (c) Zins2 testis-specific insulin homolog polypeptides which are at least 85% identical to (a) or (b); is administered to a recipient to prevent fertilization of an egg.

The invention also provides an isolated, mature rat Zins2 testis-specific insulin homolog protein according to claim 8 having: a B chain having the amino acid sequence from amino acid residue 23 to amino acid residue 51 of SEQ ID NO:2; an A chain having the amino acid sequence from amino acid residue 163 to amino acid residue 188 of SEQ ID NO:2, wherein the B chain and A chain are joined by inter- and intra-chain disulfide bonds.

Also provided is an isolated, mature human Zins2 testis-specific insulin homolog protein having: a B chain comprising amino acid residue 20 to amino acid residue 54 of SEQ ID NO:13; an A chain comprising amino acid residue 172 to amino acid residue 213 of SEQ ID NO:13; wherein the B chain and A chain are joined by inter- and intra-chain disulfide bonds.

Within another aspect the invention provides an isolated, mature rat zins2 testis-specific insulin homolog protein consisting of: a B chain having the amino acid sequence from amino acid residue 24 to amino acid residue 51 of SEQ ID NO:2; an A chain having the amino acid sequence from amino acid residue 163 to amino acid residue 188 of SEQ ID NO:2, wherein the B chain and A chain are joined by inter- and intra-chain disulfide bonds. Within a related embodiment the mature rat Zins2 testis-specific insulin homolog protein consists of: a B chain having the amino acid sequence from amino acid residue 24 to amino acid residue 52 of SEQ ID NO:2; an A chain having the amino acid sequence from amino acid residue 163 to amino acid residue 188 of SEQ ID NO:2, wherein the B chain and A chain are joined by inter- and intra-chain disulfide bonds.

The invention also provides an isolated, mature human Zins2 testis-specific insulin homolog protein consisting of: a B chain comprising amino acid residue 23 to amino acid residue 53 of SEQ ID NO:13; an A chain comprising amino acid residue 173 to amino acid residue 198 of SEQ ID NO:13; wherein the B chain and A chain are joined by inter- and intra-chain disulfide bonds. Within a related embodiment the mature human Zins2 testis-specific insulin homolog protein consists of: a B chain comprising amino acid residue 23 to amino acid residue 54 of SEQ ID NO:13; an A chain comprising amino acid residue 173 to amino acid residue 198 of SEQ ID NO:13; wherein the B chain and A chain are joined by inter- and intra-chain disulfide bonds. Within another embodiment the mature human Zins2 testis-specific insulin homolog protein consists of: a B chain comprising amino acid residue 23 to amino acid residue 54 of SEQ ID NO:13; an A chain comprising amino acid residue 173 to amino acid residue 199 of SEQ ID NO:13; wherein the B chain and A chain are joined by inter- and intra-chain disulfide bonds. Within yet another embodiment the mature human Zins2 testis-specific insulin homolog protein consists of: a B chain comprising amino acid residue 23 to amino acid residue 54 of SEQ ID NO:13; an A chain comprising amino acid residue 173 to amino acid residue 200 of SEQ ID NO:13; wherein the B chain and A chain are joined by inter- and intra-chain disulfide bonds.

Within another aspect the invention provides a method for detecting Zins2 post-translationally modified polypeptides or polypeptide fragments comprising: exposing a solution possibly containing Zins2 post-translationally modified polypeptides or polypeptide fragments to an antibody attached to a solid support, wherein said antibody binds to a first epitope of a Zins2 post-translationally modified polypeptide or polypeptide fragment; washing said immobilized antibody-polypeptide to remove unbound contaminants; exposing the immobilized antibody-polypeptide to a second antibody directed to a second epitope of a Zins2 post-translationally modified polypeptide or polypeptide fragment, wherein the second antibody is associated with a detectable label; and detecting the detectable label. Levels of Zins2 post-translationally modified polypeptides or polypeptide fragments in serum or biopsy are then correlated to tumor activity. Within a one embodiment the Zins2 post-translationally modified polypeptides or polypeptide fragments are selected from the group consisting of: a) a polypeptide consisting of the amino acid sequence from amino acid residue 53 to amino acid residue 162 of SEQ ID NO:2; b) a polypeptide consisting of the amino acid sequence from amino acid residue 55 to amino acid residue 172 of SEQ ID NO:13; c) a polypeptide consisting of the amino acid sequence from amino acid residue 201 to amino acid residue 213 of SEQ ID NO:13; and d) polypeptide fragments of a, b, or c.

Also provided is a method for detecting nucleic acid sequences encoding Zins2 post-translationally modified polypeptides or polypeptide fragments comprising: incubating a single-stranded probe molecule with RNA isolated from a biological sample under conditions of temperature and ionic strength that promote base pairing between the probe and target Zins2 RNA species; separating unbound probe from hybridized molecules; and detecting the presence of probe-Zins2 RNA hybrids. Within one embodiment the single-stranded probe molecule is at least 5 consecutive nucleotides selected from the group consisting of: a) nucleotides 157–487 of SEQ ID NO:1; b) nucleotides 179–532 of SEQ ID NO:12; and c) nucleotides 617–655 of SEQ ID NO:12.

BRIEF DESCRIPTION OF THE DRAWINGS

FIGS. 1A and 1B show a multiple alignment of human IGF I (SEQ ID NO:18), human IGF II (SEQ ID NO:19), human insulin (SEQ ID NO:20), human relaxin 2 (SEQ ID NO:21), human relaxin 1 (SEQ ID NO:22), human Leydig factor (HSLILH; SEQ ID NO:23), human INSL4 (early placenta insulin-like factor or EPIL; SEQ ID NO:24), rat Zins2 (SEQ ID NO:2), and human Zins2 (SEQ ID NO:13).

DETAILED DESCRIPTION OF THE INVENTION

Figure 1A:
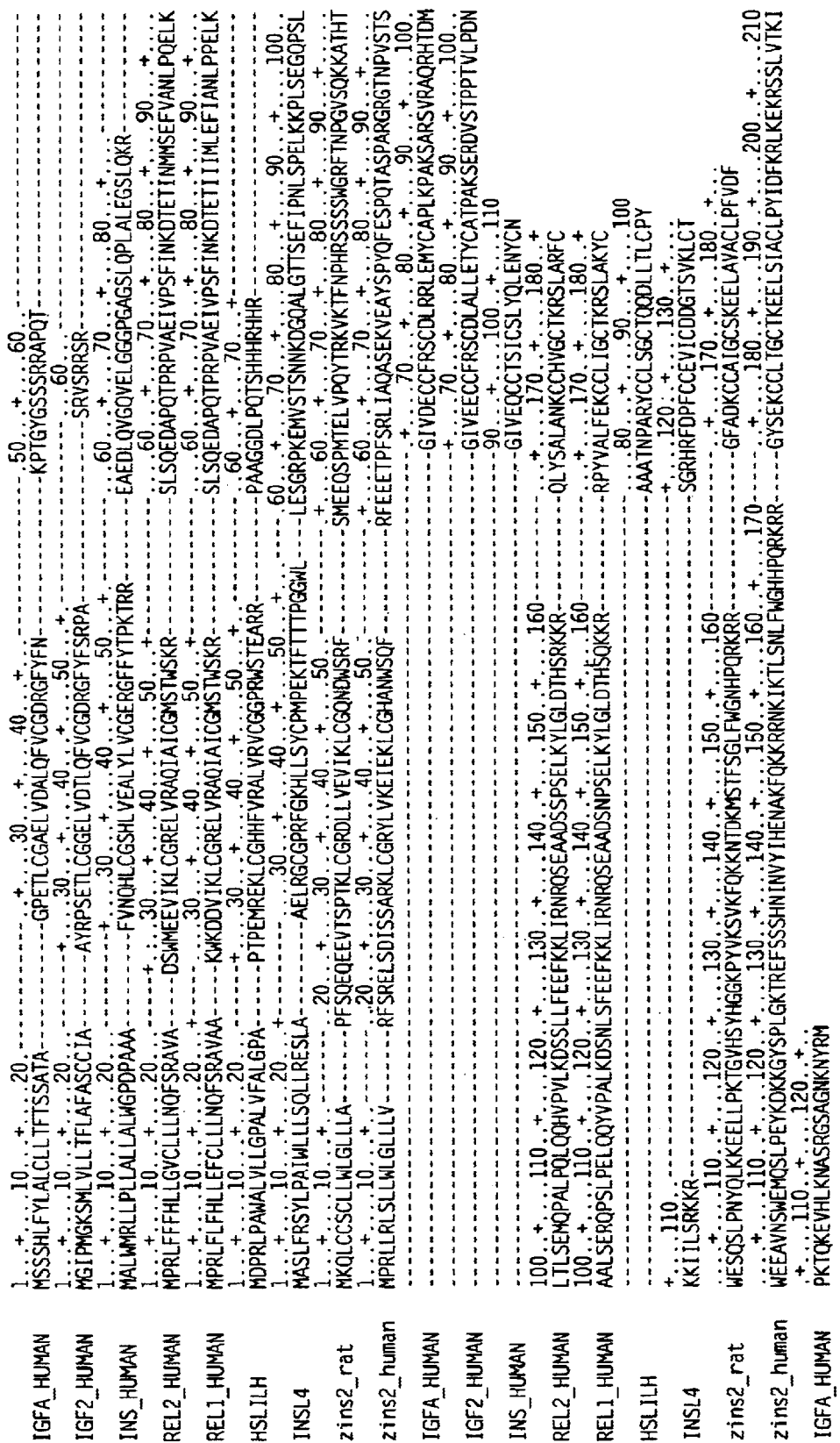

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems.

"Operably linked", when referring to DNA segments, indicates that the segments are arranged so that they function in concert for their intended purposes, e.g. transcription initiates in the promoter and proceeds through the coding segment to the terminator.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules.

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

The term "receptor" is used herein to denote a cell-associated protein, or a polypeptide subunit of such a protein, that binds to a bioactive molecule (the "ligand") and mediates the effect of the ligand on the cell. Binding of ligand to receptor results in a conformational change in the receptor (and, in some cases, receptor multimerization, i.e., association of identical or different receptor subunits) that causes interactions between the effector domain(s) and other molecules(s) in the cell. These interactions in turn lead to alterations in the metabolism of the cell. Metabolic events that are linked to receptor-ligand interactions include gene transcription, phosphorylation, dephosphorylation, cell proliferation, increases in cyclic AMP production, mobilization of cellular calcium, mobilization of membrane lipids, cell adhesion, hydrolysis of inositol lipids and hydrolysis of phospholipids. The term "receptor polypeptide" is used to denote complete receptor polypeptide chains and portions thereof, including isolated functional domains (e.g., ligand-binding domains).

A "secretory signal sequence" is a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

The present invention is based in part upon the discovery of a novel DNA sequence that encodes a polypeptide with homology to the insulin family (i.e., insulin, relaxin, Leydig factor, INSL-4, IGF I and IGF II). The DNA sequence was designated Zins2. It is also known as INSL6, the locus symbol adopted by the HUGO nomenclature committee. Analysis of the tissue distribution of the mRNA corresponding to this novel DNA showed that expression was restricted to the testis. In situ hybridization analysis demonstrated that mRNA is localized in the seminiferous tubules and epididymus, suggesting a role as a growth or differentiation factor for testis-specific cell types and involvement in sperm activation. In rat testis, zins2 RNA was detected by day and increased in intensity until day 67. Analysis of whole organ blots indicated that rat zins2 was found only in 12 month testis. Preliminary indications suggest rat zins2 is represented in pachytene spermatocytes, round spermatids and residual bodies in stage 8.

Spermatogenesis is a sequential process and takes place in the seminiferous tubules, where germ cells ultimately mature into spermatozoa, herein referred to as sperm. Testis-specific factors that influence the maturation process may come directly from the Sertoli cells that are in contact with spermatogenic cells, or may be paracrine or endocrine factors. Many of the molecules produced outside the seminiferous tubules are transported into the sperm cell microenvironment by transport and binding proteins that are expressed by the Sertoli cells within the seminiferous tubules.

Paracrine factors that cross the cellular barrier and enter the sperm cell microenvironment include molecules secreted from Leydig cells. Leydig cells are located in the interstitial space found between the seminiferous tubules, and produce several factors believed to play an important role in spermatogenic cell maturation process, such as testosterone, Leydig factor, IGF-1, inhibin and activin. The expression of these, and other factors, may be specific to a defined stage in the spermatogenic cycle. The sperm is then transported to the epididymus, where sperm motility and fertilization capacity are increased. The sperm is stored in the tail of the epididymus until released.

Before reaching the oocyte or egg and initiating an egg-sperm interaction, the sperm must be activated. The sperm undergo a gradual capacitation, lasting up to 3 or 4 hours in vitro, during which the plasma membrane of the sperm head and the outer acrosomal membrane fuse to form vesicles that facilitate the release of acrosomal enzymes. The acrosomal membrane surrounds the acrosome or acrosomal cap which is located at the anterior end of the nucleus in the sperm head.

In order for the sperm to interact with the egg the sperm must penetrate the oocyte. To enable this process the sperm must undergo acrosomal exocytosis, also known as the acrosomal reaction, and release the acrosomal enzymes in the vicinity of the oocyte. These enzymes enable the sperm to penetrate the various oocyte layers, (the cumulus oophorus, the corona radiata and the zona pellucida) and initiate an interaction with the egg. The released acrosomal enzymes include hyaluronidase and proacrosin, in addition to other enzymes such as proteases. During the acrosomal reaction, proacrosin is converted to acrosin, the active form of the enzyme, which is required for and must occur before binding and penetration of the zona pellucida is possible. A combination of the acrosomal lytic enzymes and sperm tail movements provide the sperm with the ability to penetrate the oocyte layers. Numerous sperm must reach the egg and release their acrosomal enzymes before the egg can finally be fertilized. Only one sperm will successfully bind to and penetrate the egg, after which the zona hardens so that no other sperm can penetrate and fertilization of the egg occurs (Zaneveld, in Male Infertility Chapter 11, Comhaire (Ed.), Chapman & Hall, London 1996). Insulin homologs have been associated with sperm activation and egg-sperm interaction. For instance, capacitated sperm incubated with relaxin showed an increased percentage of progressively motile sperm, increased zona penetration rates, and increased percentage of viable acrosome-reacted sperm (Carrell et al., *Endocr. Res.* 21:697–707, 1995). Homology of the Zins2 proteins with relaxin and localization of Zins2 to the testis suggests that the Zins2 proteins described herein play a role in these and other reproductive processes.

Analysis of a rat cDNA encoding a testis-specific insulin homolog (SEQ ID NO:1) revealed an opening reading frame encoding 188 amino acids (SEQ ID NO:2), comprising a putative signal sequence and a mature polypeptide. The analysis of a representative human cDNA sequence encoding a testis-specific insulin homolog polypeptide revealed a similar homology, with an open reading frame of 213 amino acids as shown in SEQ ID NO: 13.

The mature polypeptide has homology with insulin (SEQ ID NO:20), relaxin 1 (SEQ ID NO:22), relaxin 2 (SEQ ID NO:21), INSL-4 (SEQ ID NO:24) and Leydig factor (SEQ ID NO:23), respectively, as shown in FIGS. 1A and 1B. Within this family, the cysteine motif is highly conserved in the B and A chains, where the B chain motif can be represented as LCGX[10]C, where X{ } is the number of any amino acid residues except cysteine (SEQ ID NO:16). The A chain motif is CCX{3}CX{8}C, where X{ } is the number of any amino acid residues, except cysteine (SEQ ID NO:17).

Isolation of a rat cDNA sequence encoding testis-specific insulin homolog revealed that the predicted amino acid sequence contained the B chain-C peptide-A chain motif found in the relaxins and insulin. Preprorelaxin and preproinsulin both have a signal sequence, followed by the B chain, C peptide, and A chain. The mature molecule of both relaxin and insulin has the signal peptide and C peptide removed, with the B and A chains joined by both inter- and intra-chain disulfide bonds (James et al., *Nature* 267:544–546, 1977). Isolation of a human clone and subsequent-sequence analysis indicates that the human sequence (as shown in SEQ ID NO: 13) is structurally equivalent to other members of the family.

Processing of the mature protein molecule involves cleavage at the C-terminus of the signal peptide, and, based on predicted structural homology with other mature members of the insulin family, a cleavage at the C-terminus of the B chain and at the N-terminus of the A chain, resulting in removal of the C-peptide. Alignment of the rat testis-specific insulin homolog of the present invention with other known members of the insulin family (as shown in the FIGS. 1A and 1B) suggests a signal peptide cleavage site in the region of amino acid residue 22 (Glu) to amino acid residue 23 (Gln) of SEQ ID NO:2. Cleavage at the C-terminus of the B chain is predicted to be at the C-terminal of amino acid residue 52 (Arg) followed by cleavage of the Arg residue by carboxypeptidase to leave amino acid residue 51 (Ser) as the C-terminal amino acid residue. Cleavage sites resulting in the N-terminus of the A chain are suggested in the region of amino acid residue 161 (Arg) to 163 (Gly). Cleavage is predicted to be after the C-terminus of amino acid residue 162 (Arg) leaving amino acid residue 163 (Gly) as the N-terminal amino acid residue of the A chain. The C-terminal amino acid is residue 188 (Phe). The cleavage site at the junction of the C-peptide and A chain is highly conserved, occurring after Arg-X-X-Arg (wherein X is any amino acid residue), Arg-Arg or Lys-Arg; however, the cleavage sites at the junction of the signal sequence and B chain, and at the junction of the B chain and C-peptide, do not maintain a similarly high degree of conservation within the insulin family.

Alignment of a representative human testis-specific insulin homolog polypeptide suggests signal peptide cleavage in the region of amino acid residue 20 (Ser) to residue 21 (Arg) of SEQ ID NO: 13. Cleavage at the C-terminus of the B chain is predicted to be C-terminal of amino acid residue 54 (Arg), followed by cleavage of the Arg residue by a carboxypeptidase, to leave amino acid residue 53 (Phe) as the C-terminal amino acid residue of the B chain. Cleavage sites resulting in the N-terminus of the A chain are suggested in the region of amino acid residue 171 (Arg) to 173 (Gly). Cleavage is predicted to be at the C-terminus of amino acid residue 172 (Arg) leaving amino acid residue 173 (Gly) as the N-terminal amino acid residue of the A chain.

There are several potential cleavage sites in the C-terminal portion of the predicted human Zins2 A chain sequence, for example C-terminal of the Arg at amino acid residue 200 or C-terminal of the Arg at amino acid residue 205. It is not obvious based on the amino acid sequence of the human Zins2 testis-specific insulin homolog (SEQ ID NO:13) alone, or in comparison with other insulin homologs (FIGS. 1A and 1B), which site is the A chain C-terminal cleavage site, or if there would be cleavage at all. IGF-1 has a furin cleavage site and multiple potential monobasic cleavage sites and consensus furin sites in the C-terminal of the A chain, while insulin and relaxin do not. A determination of which of the two possible sites is the actual cleavage site is not possible based on the human Zins2 sequence alone. Knowledge of the amino acid sequence of the rat Zins2 homolog (SEQ ID NO:2) enables a reasonable prediction of the C-terminal cleavage site for the human A chain. Human Zins2 has two potential cleavage sites wherein rat Zins2 does not. There is a cleavage site in the human sequence C-terminal of amino acid residue 200 (Arg). Cleavage at this site, followed by cleavage of the Arg (amino acid residue 200) and Lys (amino acid residue 199) residues by a carboxypeptidase, leaves amino acid residue 198 (Phe) as the C-terminal amino acid residue of the human A chain which corresponds to the rat sequence as disclosed in SEQ ID NO:2. It is therefore predicted, based on the rat Zins2 homolog, that C-terminal cleavage site of the human Zins2 A chain would be C-terminal of amino acid residue 200 (Arg) of SEQ ID NO:13.

Based on the predicted sites, the amino acid sequence of mature human Zins2 testis-specific insulin homolog include, a B chain having the sequence of SEQ ID NO:13 from amino acid residue 21 (Arg) to amino acid residue 53 (Phe), and an A chain having the sequence of SEQ ID NO:13 from amino acid residue 173 (Gly) to amino acid residue 198 (Phe). The amino acid sequence of the mature rat Zins2 testis-specific insulin homolog include, a B chain having the sequence of SEQ ID NO:2 from amino acid residue 23 (Gln) to amino acid residue 51 (Ser), and an A chain having the sequence of SEQ ID NO:2 from amino acid residue 163 (Gly) to amino acid residue 188 (Phe). The B and A chains are joined by inter- and intra-chain disulfide bonds.

The enzymology of proinsulin conversion suggests that prohormone convertase 3 (PC3) or other homolog-monobasic capable convertases, cleave primarily at the B chain-C-peptide junction, and that prohormone convertase 2 (PC2) or similar convertases cleave preferentially at the C-peptide-A-chain junction and favor proinsulin already processed by PC3 over intact prohormone. In human and rat proinsulin, dibasic residues link the B chain and C-peptide and the C-peptide and A chain. In addition, a basic residue 4 residues N-terminal to the cleavage site (a "P4 basic residue") may be present at one or both junctions, and may influence the ability of furin, or similar convertases of the furin family such as prohormone convertase 4 (PC4) and PACE4, to cleave at the junction sites. In a study reported by Vollenweider et al. (*Diabetes* 44:1075–80, 1995), cotransfection of COS cells with PC3 and either human proinsulin, rat proinsulin II or mutant human proinsulin Arg$^{62}$ showed that PC3 cleaved both proinsulin junctions, regardless of the presence or absence of a P4 basic residue. Zins2 expression is similar to that PC4 (Seidha et al., *Mol. Endocrinol.* 6:1559–70, 1992. Co-expression within the same cell population suggests that PC4 is involved in the maturation of zins2.

Within the relaxin proteins there is a highly conserved region in the B chain of Cys-Gly-Arg and Cys-Gly at amino acid residues 35 to 37 and amino acid residues 47 to 48, respectively, that is also found in the rat testis-specific insulin homolog protein of the present invention at amino acid residues 33 to 35 and amino acid residues 45 to 46 of SEQ ID NO: 2, respectively. The equivalent region in the human sequence shown in SEQ ID NO: 13 is amino acid residues 33–35 and 45–46, respectively and is shown in the FIGS. 1A and 1B. There is evidence that residues 35–41 (CGRELVR), as found in the relaxins (and shown in the FIGS. 1A and 1B), are important for binding the relaxin receptor (Bullesbach et al., *J. Biol. Chem.* 267:22957–22960, 1992). The Zins2 testis-specific insulin homologs are missing one of the critical arginine residues, in the rat Zins2 sequence, the second arginine is replaced by valine (amino acid residue 39 of SEQ ID NO:2) and in the human Zins2 sequence, arginine is replaced by lysine (amino acid residue 39 of SEQ ID NO:13). This substitution does not rule out the possibility of cross-reactivity by the relaxins with Zins2, but it is unlikely that Zins2 would be cross-reactive with the relaxins.

Also provided by the present invention are post-translationally modified polypeptides or polypeptide fragments having the amino acid sequence from amino acid residue 53 to amino acid residue 162 of SEQ ID NO:2; the amino acid sequence from amino acid residue 55 to amino acid residue 172 of SEQ ID NO:13 or the amino acid sequence from amino acid residue 201 to amino acid residue 213 of SEQ ID NO:13. Examples of post translational modifications include proteolytic cleavage, glycosylation, disulfide bonding and hydroxylation. The C peptide from insulin, when administered to diabetic rats, decreased or prevented diabetes-induced damage to neurons or blood vessels (Ido et al., *Science* 277:563–66, 1997). Such modified polypeptides or polypeptide fragments would also be useful for diagnostic purposes, tracking the Zins2 protein, as markers for tumor activity, and the like.

Such post-translationally modified polypeptides would also be useful in applications, such as where detection has been encumbered due to Zins2 antibody cross-reactivity with other insulin homolog polypeptides. The lack of conservation within the C peptide and A chain C-terminal region among insulin homolog family members, as illustrated in FIGS. 1A and 1B, makes them ideal markers for Zins2 detection.

Chromosomal localization of the human Zins2 testis-specific insulin homolog polypeptide to chromosome 9p24 was determined using radiation hybrid chimeras. INSL4, another insulin homolog associated with reproductive tissue, was also mapped to chromosome 9p24 (Chassin et al., *Genomics* 29:465–70, 1995). Relaxin 1 and 2 were mapped to 9pter-q12 (Grawford et al., *EMBO J.* 3:2341–45, 1984). Several cases of sex reversal have been reported in association with de novo translocation or deletion involving 9p24 suggesting an association with this region and testis development (Hoo et al., *Am. J. Hum. Genet.* 45 (suppl.):A78, 1989; Bennett et al., *J. Med. Genet.* 30:518–20, 1993).

Those skilled in the art will recognize that the sequences disclosed in SEQ ID NO: 1 and SEQ ID NO: 12 represent a single allele of the rat and human testis-specific insulin homolog polypeptide, respectively, and that allelic variation, "allelic variants", and alternative splicing, "splice variants", are expected to occur. Allelic variants of the DNA sequences shown in SEQ ID NO:1 and SEQ ID NO:12, including those containing silent mutations and those in which mutations result in amino acid sequence changes, are within the scope of the present invention, as are proteins which are allelic variants of SEQ ID NO:2 and SEQ ID NO:13. Splice variants of the DNA sequences shown in SEQ ID NO:1 and SEQ ID NO:12 include DNA sequences that result from mature RNA molecules created by known eukaryotic RNA splicing processes wherein intron sequence is removed and exon sequence is joined. Such DNA sequences encoding proteins which retain properties of the Zins2 testis-specific insulin homolog proteins of SEQ ID NO:2 and SEQ ID NO:13 are within the scope of the present invention. Allelic variants and splice variants of these sequences can be cloned by probing cDNA or genomic libraries from different individuals or tissues according to standard procedures known in the art.

The present invention further provides counterpart polypeptides and polynucleotides from other species ("species homologs"). These species would include, but are not limited to, mammalian, avian, amphibian, reptile, fish, insect and other vertebrate and invertebrate species. Of particular interest are testis-specific insulin homolog polypeptides from other mammalian species, including murine, porcine, ovine, bovine, canine, feline, equine and other primate proteins. Species homologs of relaxin are unique in that there is considerable structural variation between the species, possibly resulting in functional differences between the proteins from species to species. For example, between pig, rat and human relaxins the amino acid residues can vary by greater than 50% (U.S. Pat. No. 4,835,251, incorporated herein by reference.)

Alternate species polypeptides of zins2 may have importance therapeutically. It has been demonstrated that in some cases use of a non-native protein, i.e., protein from a different species, can be more potent than the native protein. For example, salmon calcitonin has been shown to be considerably more effective in arresting bone resorption than human forms of calcitonin. There are several hypotheses as to why salmon calcitonin is more potent than human calcitonin in treatment of osteoporosis. These hypotheses include: 1) salmon calcitonin is more resistant to degradation; 2) salmon calcitonin has a lower metabolic clearance rate (MCR); and 3) salmon calcitonin may have a slightly different conformation, resulting in a higher affinity for bone receptor sites. Another example is found in the β-endorphin family (Ho et al., *Int. J. Peptide Protein Res.* 29:521–24, 1987). Studies have demonstrated that the peripheral opioid activity of camel, horse, turkey and ostrich β-endorphins is greater than that of human β-endorphins when isolated guinea pig ileum was electrostimulated and contractions were measured. Vas deferens from rat, mouse and rabbit were assayed as well. In the rat vas deferens model, camel and horse β-endorphins showed the highest relative potency. Synthesized rat relaxin was as active as human and porcine relaxin in the mouse symphysis pubis assay (Bullesbach and Schwabe, *Eur. J. Biochem.* 241:533–7, 1996). Thus, the rat zins2 molecules of the present invention may have higher potency than the human endogenous molecule in human cells, tissues and recipients.

Species homologs of the rat and human testis-specific insulin homolog polypeptides can be cloned using information and compositions provided by the present invention, in combination with conventional cloning techniques. For example, a cDNA can be cloned using mRNA obtained from a tissue or cell type that expresses the protein. Suitable sources of mRNA can be identified by probing Northern blots with probes designed from the sequences disclosed herein. A library is then prepared from mRNA of a positive tissue cell line. A testis-specific insulin homolog-encoding cDNA can then be isolated by a variety of methods, such as by probing with a complete or partial rat cDNA or with one or more sets of degenerate probes based on the disclosed sequences. A cDNA can also be cloned using the polymerase chain reaction, or PCR (Mullis, U.S. Pat. No. 4,683,202), using primers designed from the sequences disclosed herein. Within an additional method, the cDNA library can be used to transform or transfect host cells, and expression of the cDNA of interest can be detected with an antibody to the testis-specific insulin homolog protein or polypeptide. Similar techniques can also be applied to the isolation of genomic clones.

The present invention also provides isolated testis-specific insulin homolog polypeptides that are substantially homologous to the polypeptides of SEQ ID NO: 2, SEQ ID NO:13 and their species homologs. By "isolated" is meant a protein or polypeptide which is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. The term "substantially homologous" is used herein to denote polypeptides having 50%, preferably 70%, more preferably at least 85%, sequence identity to the sequences shown in SEQ ID NO: 2, SEQ ID NO: 13, or their species homologs. Such polypeptides will more preferably be at least 90% identical, and most preferably 95% or more identical to SEQ ID NO: 2, SEQ ID NO: 13, or their species homologs. Percent sequence identity is determined by conventional methods. See, for example, Altschul et al., *Bull. Math. Bio.* 48: 603–616, 1986 and Henikoff and Henikoff, *Proc. Natl. Acad. Sci. USA* 89:10915–10919, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown in Table 1 (amino acids are indicated by the standard one-letter codes).

The percent identity of the optimal alignment is then calculated as:

$$\frac{\text{Total number of identical matches}}{[\text{length of the longer sequence plus the number of gaps introduced into the longer sequence in order to align the two sequences}]} \times 100$$

TABLE 1

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

Sequence identity of polynucleotide molecules is determined by similar methods using a ratio as disclosed above.

Substantially homologous proteins and polypeptides are characterized as having one or more amino acid substitutions, deletions or additions. These changes are preferably of a minor nature, that is conservative amino acid substitutions (see Table 2) and other substitutions that do not significantly affect the folding or activity of the protein or polypeptide; small deletions, typically of one to about 30 amino acids; and small amino- or carboxyl-terminal extensions, such as an amino-terminal methionine residue, a small linker peptide of up to about 20–25 residues, or a small extension that facilitates purification, such as a polyhistidine tract, an antigenic epitope or a-binding domain. See, in general Ford et al., *Protein Expression and Purification* 2: 95–107, 1991, which is incorporated herein by reference.

TABLE 2

Conservative amino acid substitutions

| | |
|---|---|
| Basic | arginine |
| | lysine |
| | histidine |
| Acidic | glutamic acid |
| | aspartic acid |
| Polar | glutamine |
| | asparagine |
| Hydrophobic | leucine |
| | isoleucine |
| | valine |
| Aromatic | phenylalanine |
| | tryptophan |
| | tyrosine |
| Small | glycine |
| | alanine |
| | serine |
| | threonine |
| | methionine |

The proteins of the present invention can also comprise, in addition to the 20 standard amino acids, non-naturally occurring amino acid residues. Non-naturally occurring amino acids include, without limitation, trans-3-methylproline, 2,4-methanoproline, cis-4-hydroxyproline, trans-4-hydroxyproline, N-methyl-glycine, allo-threonine, methylthreonine, hydroxyethyl-cysteine, hydroxyethylhomocysteine, nitroglutamine, homoglutamine, pipecolic acid, tert-leucine, norvaline, 2-azaphenylalanine, 3-azaphenylalanine, 4-azaphenylalanine, 4-fluorophenylalanine, 4-hydroxyproline, 6-N-methyl lysine, 2-aminoisobutyric acid, isovaline and α-methyl serine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations are carried out in a cell free system comprising an *E. coli* S30 extract and commercially available enzymes and other reagents. Proteins are purified by chromatography. See, for example, Robertson et al., *J. Am. Chem. Soc.* 113:2722, 1991; Ellman et al., *Meth. Enzymol.* 202:301, 1991; Chung et al., *Science* 259:806–09, 1993; and Chung et al., *Proc. Natl. Acad. Sci. USA* 90:10145–49, 1993). In a second method, translation is carried out in xenopus oocytes by microinjection of mutated mRNA and chemically aminoacylated suppressor tRNAs (Turcatti et al., *J. Biol. Chem.* 271:19991–98, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470–76, 1994. Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395–403, 1993).

A limited number of non-conservative amino acids, amino acids that are not encoded by the genetic code, non-naturally occurring amino acids, and unnatural amino acids may be substituted for amino acid residues in the polypeptides of the present invention. "Unnatural amino acids" have been modified after protein synthesis, and/or have a chemical structure in their side chain(s) different from that of the standard amino acids. Unnatural amino acids can be chemically synthesized, or preferably, are commercially available, and include pipecolic acid, thiazolidine carboxylic acid, dehydroproline, 3- and 4-methylproline, and 3,3-dimethylproline.

Essential amino acids in the polypeptides of the present invention can be identified according to procedures known in the art, such as site-directed mutagenesis or alanine-scanning mutagenesis (Cunningham and Wells, *Science* 244, 1081–1085, 1989). In the latter technique, single alanine mutations are introduced at every residue in the molecule, and the resultant mutant molecules are tested for biological activity. (e.g. proliferation or differentiation) to identify amino acid residues that are critical to the activity of the molecule.

Multiple amino acid substitutions can be made and tested using known methods of mutagenesis and screening, such as those disclosed by Reidhaar-Olson and Sauer (*Science* 241:53–57, 1988) or Bowie and Sauer (*Proc. Natl. Acad. Sci. USA* 86:2152–2156, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832–10837, 1991; Ladner et al., U.S. Pat. No. 5,223,409; Huse, WIPO Publication WO 92/06204) and region-directed mutagenesis (Derbyshire et al., *Gene* 46:145, 1986; Ner et al., *DNA* 7:127, 1988).

Mutagenesis methods as disclosed above can be combined with high-throughput, automated screening methods to detect activity of cloned, mutagenized polypeptides in host cells. Mutagenized DNA molecules that encode active polypeptides (e.g., stimulation of proliferation or differentiation of testicular cells) can be recovered from the host cells and rapidly sequenced using modern equipment. These methods allow the rapid determination of the importance of individual amino acid residues in a polypeptide of interest, and can be applied to polypeptides of unknown structure.

Using the methods discussed above, one of ordinary skill in the art can prepare a variety of polypeptides that are substantially homologous to residues 1 to 188 of SEQ ID NO: 2, residues 1 to 213 of SEQ ID NO: 13, or allelic variants thereof and retain the activity of the wild-type protein.

The polypeptides of the present invention, including full-length proteins and fragments thereof, can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly culture cells of multicellular organisms, are preferred. Techniques for manipulating cloned DNA molecules and introducing exogenous DNA into a variety of host cells are disclosed by Sambrook et al., *Molecular Cloning: A Laboratory Manual,* 2nd ed., Cold Spring Harbor Laboratory Press, Cold Spring Harbor, N.Y., 1989, and Ausubel et al., ibid., which are incorporated herein by reference.

In general, a DNA sequence encoding a testis-specific insulin homolog polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To insure cleavage of the B and A chains, cells transfected with expression vectors containing DNA sequences encoding testis-specific insulin homologs are co-transfected with expression vectors encoding a suitable prohormone convertase, for example furin, PC4, PC2 or PC3. Such sequences are known in the art and can be inserted into expression vectors and transfected into cells as described herein.

To direct a testis-specific insulin homolog polypeptide into the secretory pathway of a host cell, a secretory signal sequence (also known as a leader sequence, prepro sequence or pre sequence) is provided in the expression vector. The secretory signal sequence may be that of the testis-specific insulin homolog polypeptide, or may be derived from another secreted protein (e.g., t-PA) or synthesized de novo. The secretory signal sequence is joined to the testis-specific insulin homolog DNA sequence in the correct reading frame. Secretory signal sequences are commonly positioned 5' to the DNA sequence encoding the polypeptide of interest, although certain signal sequences may be positioned elsewhere in the DNA sequence of interest (see, e.g., Welch et al., U.S. Pat. No. 5,037,743; Holland et al., U.S. Pat. No. 5,143,830).

Cultured mammalian cells are also preferred hosts within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology* 52;456, 1973), electroporation (Neumann et al., *EMBO J.* 1:841–845, 1982), DEAE-dextran mediated transfection (Ausubel et al., eds., *Current Protocols in Molecular Biology,* John Wiley and Sons, Inc., NY, 1987), and liposome-mediated transfection (Hawley-Nelson et al., *Focus* 15:73, 1993; Ciccarone et al., *Focus* 15:80, 1993), which are incorporated herein by reference. The production of recombinant polypeptides in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134, which are incorporated herein by reference. Preferred cultured mammalian cells include BHK 570 cells (ATCC accession no.10314), COS-1 (ATCC No. CRL 1650), COS-7 (ATCC No. CRL 1651), 293 (ATCC No. CRL 1573; Graham et al., *J. Gen. Virol.* 36:59–72, 1977) and Chinese hamster ovary (e.g. CHO-K1; ATCC No. CCL 61) cell lines. Additional suitable cell lines are known in the art and available from public depositories such as the American Type Culture Collection, Rockville, Md. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978, which are incorporated herein by reference) and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable-transfectants." A preferred selectable marker is a gene encoding resistance to the antibiotic neomycin. Selection is carried out in the presence of a neomycin-type drug, such as G-418 or the like. Selection systems may also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g. hygromycin resistance, multi-drug resistance, puromycin acetyltransferase) can also be used.

Other higher eukaryotic cells can also be used as hosts, including insect cells, plant cells and avian cells. Transformation of insect cells and production of foreign polypeptides therein is disclosed by Guarino et al., U.S. Pat. No. 5,162,222; Bang et al., U.S. Pat. No. 4,775,624; and WIPO publication WO 94/06463, which are incorporated herein by reference. The use of *Agrobacterium rhizogenes* as a vector for expressing genes in plant cells has been reviewed by Sinkar et al., *J. Biosci.* (*Bangalore*) 11:47–58, 1987.

Fungal cells, including yeast cells, and particularly cells of the genus Saccharomyces, can also be used within the present invention, such as for producing testis-specific insulin homolog fragments or polypeptide fusions. Methods for transforming yeast cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075, which are incorporated herein by reference. Transformed cells are selected by phenotype determined by the selectable marker, commonly drug resistance or the ability to grow in the absence of a particular nutrient (e.g. leucine). A preferred vector system for use in yeast is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092, which are incorporated herein by reference) and alcohol dehydrogenase genes. See also U.S. Pat. Nos. 4,990,446; 5,063,154; 5,139,936 and 4,661,454, which are incorporated herein by reference. Transformation systems for other yeasts, including *Hansenula polymorpha, Schizosaccharomyces pombe, Kluyveromyces lactis, Kluyveromyces fragilis, Ustilago maydis, Pichia pastoris, Pichia guillermondii* and *Candida maltosa* are known in the art. See, for example, Gleeson et al., *J. Gen. Microbiol.* 132:3459–3465, 1986 and Cregg, U.S. Pat. No. 4,882,279. Aspergillus cells may be utilized according to the methods of McKnight et al., U.S. Pat. No. 4,935,349, which is incorporated herein by reference. Methods for transforming *Acremonium chrysogenum* are disclosed by Sumino et al., U.S. Pat. No. 5,162,228, which is incorporated herein by reference. Methods for transforming Neurospora are disclosed by Lambowitz, U.S. Pat. No. 4,486,533, which is incorporated herein by reference.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell.

Testis-specific insulin homolog polypeptides can also be used to prepare antibodies that specifically bind to testis-specific insulin homolog epitopes, peptides or polypeptides. Methods for preparing polyclonal and monoclonal antibodies are well known in the art (see, for example, Sambrook et al., *Molecular Cloning: A Laboratory Manual, Second Edition,* Cold Spring Harbor, N.Y., 1989; and Hurrell, J. G. R., Ed., *Monoclonal Hybridoma Antibodies: Techniques and Applications,* CRC Press, Inc., Boca Raton, Fla., 1982, which are incorporated herein by reference). As would be evident to one of ordinary skill in the art, polyclonal antibodies can be generated from a variety of warm-blooded animals, such as horses, cows, goats, sheep, dogs, chickens, rabbits, mice, and rats.

The immunogenicity of a testis-specific insulin homolog polypeptide may be increased through the use of an adjuvant, such as alum (aluminum hydroxide) or Freund's complete or incomplete adjuvant. Polypeptides useful for immunization also include fusion polypeptides, such as fusions of testis-specific insulin homolog or a portion thereof with an immunoglobulin polypeptide or with maltose binding protein. The polypeptide immunogen may be a full-length molecule or a portion thereof. If the polypeptide portion is "hapten-like", such portion may be advantageously joined or linked to a macromolecular carrier (such as keyhole limpet hemocyanin (KLH), bovine serum albumin (BSA) or tetanus toxoid) for immunization.

As used herein, the term "antibodies" includes polyclonal antibodies, affinity-purified polyclonal antibodies, monoclonal antibodies, and antigen-binding fragments, such as F(ab')$_2$ and Fab proteolytic fragments. Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting only non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced. Alternative techniques for generating or selecting antibodies useful herein include in vitro exposure of lymphocytes to testis-specific insulin homolog protein or peptide, and selection of antibody display libraries in phage or similar vectors (for instance, through use of immobilized or labeled testis-specific insulin homolog protein or peptide).

Antibodies are defined to be specifically binding if they bind to a testis-specific insulin homolog polypeptide with a binding affinity ($K_a$) of $10^6$ M$^{-1}$ or greater, preferably $10^7$ M$^{-1}$ or greater, more preferably $10^8$ M$^{-1}$ or greater, and most preferably $10^9$ M$^{-1}$ or greater. The binding affinity of an antibody can be readily determined by one of ordinary skill in the art (for example, by Scatchard analysis).

A variety of assays known to those skilled in the art can be utilized to detect antibodies which specifically bind to testis-specific insulin homolog proteins or peptides. Exemplary assays are described in detail in *Antibodies: A Laboratory Manual,* Harlow and Lane (Eds.), Cold Spring Harbor Laboratory Press, 1988. Representative examples of such assays include: concurrent immunoelectrophoresis, radioimmunoassay, radioimmuno-precipitation, enzyme-linked immunosorbent assay (ELISA), dot blot or Western blot assay, inhibition or competition assay, and sandwich assay. In addition, antibodies can be screened for binding to wild-type versus mutant testis-specific insulin homolog protein or peptide.

Antibodies to testis-specific insulin homolog polypeptides may be used for tagging cells that express testis-specific insulin homolog polypeptides; for isolating testis-specific insulin homolog polypeptides by affinity purification; for diagnostic assays for determining circulating levels of testis-specific insulin homolog polypeptides; for detecting or quantitating soluble testis-specific insulin homolog polypeptides as marker of underlying pathology or disease; in analytical methods employing FACS; for screening expression libraries; for generating anti-idiotypic antibodies; and as neutralizing antibodies. Suitable direct tags or labels include radionuclides, enzymes, substrates, cofactors, inhibitors, fluorescent markers, chemiluminescent markers, magnetic particles and the like; indirect tags or labels may feature use of biotin-avidin or other complement/anti-complement pairs as intermediates. Antibodies herein may also be directly or indirectly conjugated to drugs, toxins, radionuclides and the like, and these conjugates used for in vivo diagnostic or therapeutic applications.

Testis-specific insulin homolog polypeptide prepared according to the present invention is purified using methods generally known in the art, such as affinity purification and separations based on size, charge, solubility and other properties of the protein. When the protein is produced in cultured mammalian cells, it is preferred to culture the cells in a serum-free culture medium in order to limit the amount of contaminating protein. The medium is harvested and fractionated. Preferred methods of fractionation include affinity chromatography, Q-Fast Flow Sepharose, MonoQ resin, FPLC, phenyl Sepharose, hydroxyapatite, Mono S and/or S-Sepharose. Proteins can also be purified using an immobilized an affinity tag (e.g., polyhistidine, substance P or other polypeptide or protein for which an antibody or other specific binding agent is available). A specific cleavage site may be provided between the protein of interest and the affinity tag. Preferred affinity tags include polyhistidine tail, which permits purification of the fusion protein on immobilized nickel (Houchuli et al., *Bio/Technol.* 6:1321–1325, 1988). In prokaryotic expression systems, a maltose binding protein (MBP) fusion may be advantageously used as an affinity tag. If the protein is to be recovered from the cytoplasm or periplasm of the host cells, the cells are first disrupted, and a crude extract containing the protein is recovered and subjected to further purification steps. Secreted protein is recovered from cell-conditioned media, preferably after concentration of the conditioned media. Selection of particular fractionation steps and the sequence of those steps will be based in part of the type of host cell and the expression system chosen. Such determinations are within the level of ordinary skill in the art.

Methods for preparing polyclonal and monoclonal antibodies are well known in the art (see for example, Sambrook et al., *Molecular Cloning: A Laboratory Manual, Second Edition,* Cold Spring Harbor, N.Y., 1989; and Hurrell, J. G. R., Ed., *Monoclonal Hybridoma Antibodies: Techniques and Applications,* CRC Press, Inc., Boca Raton, Fla., 1982, which are incorporated herein by reference). As would be evident to one of ordinary skill in the art, polyclonal antibodies can be generated from a variety of warm-blooded animals such as horses, cows, goats, sheep, dogs, chickens, rabbits, mice, and rats. The immunogenicity of a testis-specific insulin homolog polypeptide may be increased through the use of an adjuvant such as Freund's complete or incomplete adjuvant.

Antibodies to testis-specific insulin homolog polypeptide may be used for isolating, for affinity purification, for diagnostic assays for determining circulating levels of testis-specific insulin homolog polypeptides, and as antagonists to block testis-specific insulin homolog binding and signal transduction in vitro and in vivo. These antibodies would be useful as contraceptives to prevent fertilization of an egg. Such antibodies could act as antagonists by inhibiting a component(s) of spermatogenesis and/or sperm activation. Such antibody "antagonists" can be used for contraception in animals, and in particular, domestic animals and livestock. For instance, anti-Zins2 immunization could be used in place of surgical forms of contraception (such as spaying and neutering), and would allow for the possibility of future breeding if desired.

Genes encoding polypeptides having potential Zins2 testis-specific insulin homolog polypeptide binding domains can be obtained by screening random peptide libraries displayed on phage (phage display) or on bacteria, such as *E. coli.* Nucleotide sequences encoding the polypeptides can be obtained in a number of ways, such as through random mutagenesis and random polynucleotide synthesis. These random peptide display libraries can be used to screen for peptides which interact with a known target which can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. 5,223,409; Ladner et al., U.S. Pat. No. 4,946,778; Ladner et al., U.S. Pat. No. 5,403,484 and Ladner et al., U.S. Pat. No. 5,571,698) and random peptide display libraries and kits for screening such libraries are available commercially, for instance from Clontech (Palo Alto, Calif.), Invitrogen Inc. (San Diego, Calif.), New England Biolabs, Inc. (Beverly, Mass.) and Pharmacia LKB Biotechnology Inc. (Piscataway, N.J.). Random peptide display libraries can be screened using the Zins2 testis-specific insulin homolog sequences disclosed herein to identify proteins which bind to Zins2. These "binding proteins" which interact with Zins2 testis-specific insulin homolog polypeptides may be used for tagging cells; for isolating homolog polypeptides by affinity purification; they can be directly or indirectly conjugated to drugs, toxins, radionuclides and the like. These binding proteins can also be used in analytical methods such as for screening expression libraries and neutralizing activity. The binding proteins can also be used for diagnostic assays for determining circulating levels of polypeptides; for detecting or quantitating soluble polypeptides as marker of underlying pathology or disease. These binding proteins can also act as zins2 "antagonists" to block testis-specific insulin homolog binding and signal transduction in vitro and in vivo. These anti-Zins2 binding proteins would be useful for inhibiting spermatogenesis and sperm activation. Such anti-Zins2 binding proteins can be used for contraception in humans and animals, and in particular, domestic animals and livestock, where they act to prevent fertilization of an egg. Such anti-Zins2 binding proteins could be used, for instance, in place of surgical forms of contraception (such as spaying and neutering), and would allow for the possibility of future breeding of treated animals if desired.

A variety of assays known to those skilled in the art can be utilized to detect antibodies or binding proteins which specifically bind to testis-specific insulin homolog proteins or peptides. Exemplary assays are described in detail in *Antibodies: A Laboratory Manual,* Harlow and Lane (Eds.), Cold Spring Harbor Laboratory Press, 1988. Representative examples of such assays include: concurrent immunoelectrophoresis, radio-immunoassays, radio-immunoprecipitations, enzyme-linked immunosorbent assays (ELISA), dot blot or Western blot assays, inhibition or competition assays, and sandwich assays. A preferred assay system employing a ligand-binding receptor fragment uses a commercially available biosensor instrument (BIAcore™, Pharmacia Biosensor, Piscataway, N.J.), wherein the receptor fragment is immobilized onto the surface of a receptor chip. Use of this instrument is disclosed by Karlsson, *J. Immunol. Methods* 145:229–240, 1991 and Cunningham and Wells, *J. Mol. Biol.* 234:554–563, 1993. A receptor fragment is covalently attached, using amine or sulfhydryl chemistry, to dextran fibers that are attached to gold film within the flow cell. A test sample is passed through the cell. If ligand is present in the sample, it will bind to the immobilized receptor polypeptide, causing a change in the refractive index of the medium, which is detected as a change in surface plasmon resonance of the gold film. This system allows the determination of on- and off-rates, from which binding affinity can be calculated, and assessment of stoichiometry of binding.

Molecules of the present invention can be used to identify and isolate receptors for testis-specific insulin homolog polypeptides. For example, proteins and peptides of the present invention can be immobilized on a column and membrane preparations run over the column (*Immobilized Affinity Ligand Techniques,* Hermanson et al., eds., Academic Press, San Diego, Calif., 1992, pp.195–202). Proteins and peptides can also be radiolabeled (*Methods in Enzymol.,* vol. 182, "Guide to Protein Purification", M. Deutscher, ed., Acad. Press, San Diego, 1990, 721–737) or photoaffinity labeled (Brunner et al., *Ann. Rev. Biochem.* 62:483–514, 1993 and Fedan et al., *Biochem. Pharmacol.* 33:1167–1180, 1984) and specific cell-surface proteins can be identified.

Polypeptides of the present invention are used to stimulate proliferation or differentiation of testicular cells. Proliferation and differentiation can be measured using cultured testicular cells or in vivo by administering molecules of the present invention to the appropriate animal model. Cultured testicular cells include dolphin DB1.Tes cells (CRL-6258); mouse GC-1 spg cells (CRL-2053); TM3 cells (CRL-1714); TM4 cells (CRL-1715); and pig ST cells (CRL-1746), available from American Type Culture Collection, 12301 Parklawn Drive, Rockville, Md. Assays measuring cell proliferation or differentiation are well known in the art. For example, assays measuring proliferation include such assays as chemosensitivity to neutral red dye (Cavanaugh et al., *Investigational New Drugs* 8:347–354, 1990, incorporated herein by reference), incorporation of radiolabelled nucleotides (Cook et al., *Analytical Biochem.* 179:1–7, 1989, incorporated herein by reference), incorporation of 5-bromo-2'-deoxyuridine (BrdU) in the DNA of proliferating cells (Porstmann et al., *J. Immunol. Methods* 82:169–179, 1985, incorporated herein by reference), and use of tetrazolium salts (Mosmann, *J. Immunol. Methods* 65:55–63, 1983; Alley et al., *Cancer Res.* 48:589–601, 1988; Marshall et al., *Growth Reg.* 5:69–84, 1995; and Scudiero et al., *Cancer Res.* 48:4827–4833, 1988; all incorporated herein by reference). Assays measuring differentiation include, for example, measuring cell-surface markers associated with stage-specific expression of a tissue, enzymatic activity, functional activity or morphological changes (Watt, *FASEB*, 5:281–284, 1991; Francis, *Differentiation* 57:63–75, 1994; Raes, *Adv. Anim. Cell Biol. Technol. Bioprocesses*, 161–171, 1989; all incorporated herein by reference).

In vivo assays for evaluating the effect of testis-specific insulin homolog polypeptide on testes are well known in the art. For example, compounds can be injected intraperitoneally for a specific time duration. After the treatment period, animals are sacrificed and testes removed and weighed. Testicles are homogenized and sperm head counts are made (Meistrich et al., *Exp. Cell Res.* 99:72–78, 1976; incorporated herein by reference).

Other activities, for example, chemotaxic activity that may be associated with proteins of the present invention can be analyzed. For example, late stage factors in spermatogenesis may be involved in egg-sperm interactions and sperm motility. Activities, such as enhancing viability of cryopreserved sperm, stimulating the acrosome reaction, enhancing sperm motility and enhancing egg-sperm interactions may be associated with the proteins of the present invention. Assays evaluating such activities are known (Rosenberger, *J. Androl.* 11:89–96, 1990; Fuchs, *Zentralbl Gynakol* 11:117–120, 1993; Neurwinger et al., *Andrologia* 22:335–9, 1990; Harris et al., *Human Reprod.* 3:856–60, 1988; and Jockenhovel, *Andrologia* 22:171–178, 1990; Lessing et al., *Fertil. Steril.* 44:406–9 (1985); Zaneveld, In Male Infertility Chapter 11, Comhaire Ed., Chapman & Hall, London 1996; all incorporated herein by reference). These activities are expected to result in enhanced fertility and successful reproduction.

Accordingly, proteins of the present invention may have applications in enhancing fertilization during assisted reproduction in humans and in animals. Such assisted reproduction methods are known in the art and include artificial insemination, in vitro fertilization, embryo transfer and gamete intrafallopian transfer. Such methods are useful for assisting men and women who may have physiological or metabolic disorders that prevent natural conception. They may be used to enable women who wish to bear children but do not wish to, or are unable to conceive naturally. Such methods are also used in animal breeding programs, such as for livestock breeding and could be used as methods for the creation of transgenic animals. Proteins of the present invention can be combined with sperm, an egg or an egg-sperm mixture prior to fertilization of the egg. In some species, sperm capacitate spontaneously during in vitro fertilization procedures, but normally sperm capacitate over an extended period of time both in vivo and in vitro. It is advantageous to increase sperm activation during such procedures to enhance the likelihood of successful fertilization. The washed sperm or sperm removed from the seminal plasma used in such assisted reproduction methods has been shown to have altered reproductive functions, in particular, reduced motility and zona interaction. To enhance fertilization during assisted reproduction methods sperm is capacitated using exogenously added compounds. Suspension of the sperm in seminal plasma from normal subjects or in a "capacitation media" containing a cocktail of compounds known to activate sperm, such as caffeine, dibutyl cyclic adenosine monophosphate (dbcAMP) or theophylline, have resulted in improved reproductive function of the sperm, in particular, sperm motility and zonae penetration (Park et al., *Am. J. Obstet. Gynecol.* 158:974–9, 1988; Vandevoort et al., *Mol. Repro. Develop.* 37:299–304, 1993; Vandevoort and Overstreet, *J. Androl.* 16:327–33, 1995). The presence of immunoreactive relaxin in vivo and in association with cryopreserved semen, was shown to significantly increase sperm motility (Juang et al., *Anim. Reprod. Sci.* 20:21–9, 1989; Juang et al., *Anim. Reprod. Sci.* 22:47–53, 1990). Porcine relaxin stimulated sperm motility in cryopreserved human sperm (Colon et al., *Fertil. Steril.* 46:1133–39, 1986; Lessing et al., *Fertil. Steril.* 44:406–9, 1985) and preserved ability of washed human sperm to penetrate cervical mucus in vitro (Brenner et al., *Fertil. Steril.* 42:92–6, 1984, all incorporated herein by reference). Polypeptides of the present invention can used in such methods to enhance viability of cryopreserved sperm, enhance sperm motility and enhance fertilization, particularly in association with methods of assisted reproduction.

In cases where pregnancy is not desired, Zins2 proteins or protein fragments may function as germ-cell-specific antigens for use as components in "immunocontraceptive" or "anti-fertility vaccines to induce formation of antibodies and/or cell mediated immunity to selectively inhibit a process, or processes, critical to successful reproduction in humans and animals. The use of sperm and testis antigens in the development of an immunocontraceptive have been described (O'Hern et al., *Biol Reprod.* 52:311–39, 1995; Diekman and Herr, *Am. J. Reprod. Immunol.* 37:111–17, 1997; Zhu and Naz, *Proc. Natl. Acad. Sci. USA* 94:4704–9, 1997, all of which are incorporated herein by reference). A vaccine based on human chorionic gonadotrophin (HCG) linked to a diphtheria or tetanus carrier is currently in clinical trials (Talwar et al., *Proc. Natl. Acad. Sci. USA* 91:8532–36, 1994, incorporated herein by reference). A single injection resulted in production of high titer antibodies that persisted for nearly a year in rabbits (Stevens, *Am. J. Reprod. Immunol.* 29:176–88, 1993, incorporated herein by reference). Such methods of immunocontraception using vaccines would include a Zins2 testes-specific insulin homolog protein or fragment thereof. The Zins2 protein or fragments can be conjugated to a carrier protein or peptide, such as tetanus or diphtheria toxoid. An adjuvant, as described above, can be included and the protein or fragment can be noncovalently associated with other molecules to enhance intrinsic immunoreactivity. Methods for administration and methods for determining the number of administrations are known in the art. Such a method might include a number of primary injections over several weeks followed by booster injections as needed to maintain a suitable antibody titer.

Regulation of reproductive function in males and females is controlled in part by feedback inhibition of the hypothalamus and anterior pituitary by blood-bone hormones. Testis proteins, such as activins and inhibins, have been shown to regulate secretion of active molecules including follicle stimulating hormone (FSH) for the pituitary (Ying, *Endodcr. Rev.* 9:267–93, 1988; Plant et al., *Hum. Reprod.* 8:41–44, 1993). Inhibins, also expressed in the ovaries, have also been shown to regulate ovarian functions (Woodruff et al., *Endocr.* 132:2332–42,1993; Russell et al., *J. Reprod. Fertil.* 100:115–22, 1994). Relaxin has also been shown to be a systemic and local acting hormone regulating follicular and uterine growth (Bagnell et al., *J. Reprod. Fertil.* 48:127–38, 1993), as such, the polypeptides of the present invention may also have effects on female gametes and reproductive tract. These functions may also be associated with the Zins2 proteins and may be used to regulate testicular or ovarian functions.

Post-translationally modified polypeptides or polypeptide fragments, such as the C peptide and the C-terminal region of the A chain, polypeptides having the amino acid sequence from amino acid residue 53 to amino acid residue 162 of SEQ ID NO:2; the amino acid sequence from amino acid residue 55 to amino acid residue 172 of SEQ ID NO:13 or the amino acid sequence from amino acid residue 201 to amino acid residue 213 of SEQ ID NO:13 would also be useful for diagnostic purposes as markers for tumor activity, tracking the Zins2 protein, and the like.

A diagnostic method of the present invention involves the detection of post-translationally modified polypeptides or polypeptide fragments, such as the Zins2 C peptide and the C-terminal region of the Zins2 A chain, in the serum or tissue biopsy. Such post-translationally modified polypeptides can be detected, for example, using immunoassay techniques and antibodies capable of recognizing a Zins2 post-translationally modified polypeptides or polyp eptide fragments epitope. More specifically, the present invention contemplates methods for detecting Zins2 post-translationally modified polypeptides or polypeptide fragments comprising: exposing a solution possibly containing Zins2 post-translationally modified polypeptides or polypeptide fragments to an antibody attached to a solid support, wherein said antibody binds to a first epitope of a Zins2 post-translationally modified polypeptide or polypeptide fragment; washing said immobilized antibody-polypeptide to remove unbound contaminants; exposing the immobilized antibody-polypeptide to a second antibody directed to a second epitope of a Zins2 post-translationally modified polypeptide or polypeptide fragment, wherein the second antibody is associated with a detectable label; and detecting the detectable label. Levels of Zins2 post-translationally modified polypeptides or polypeptide fragments in serum or biopsy are then correlated to tumor activity.

Nucleic acid molecules disclosed herein can be used to detect the expression of a Zins2 gene in a biological sample. Such probe molecules include double-stranded nucleic acid molecules comprising the nucleotide sequences of SEQ ID NOs:1 or 12, or fragments thereof, as well as single-stranded nucleic acid molecules having the complement of the nucleotide sequences of SEQ ID NOs:1 or 12, or a fragment thereof. Probe molecules may be DNA, RNA, oligonucleotides, and the like.

In a basic assay, a single-stranded probe molecule is incubated with RNA, isolated from a biological sample, under conditions of temperature and ionic strength that promote base pairing between the probe and target Zins2 RNA species. After separating unbound probe from hybridized molecules, the amount of hybrids is detected. Well-established hybridization methods of RNA detection include northern analysis and dot/slot blot hybridization (see, for example, Ausubel ibid. and Wu et al. (eds.), "Analysis of Gene Expression at the RNA Level," in *Methods in Gene Biotechnology*, pages 225–239 (CRC Press, Inc. 1997)). Suitable probes include nucleic acid molecules that bind with a portion of a Zins2 post-translationally modified polypeptide or polypeptide fragment. Such probes can be RNA or DNA. DNA can be either cDNA or genomic DNA. Polynucleotide probes are single or double-stranded DNA or RNA, generally synthetic oligonucleotides, but may be generated from cloned cDNA or genomic sequences or its complements. Analytical probes will generally be at least 20 nucleotides in length, although somewhat shorter probes (14–17 nucleotides) can be used. PCR primers are at least 5 nucleotides in length, preferably 15 or more nt, more preferably 20–30 nt. Short polynucleotides can be used when a small region of the gene is targeted for analysis. For gross analysis of genes, a polynucleotide probe may comprise an entire exon or more. Exemplarily probes include those containing at least 5 consecutive nucleotides from nucleotides 157–487 of SEQ ID NO:1. nucleotides 179–532 of SEQ ID NO:12 or nucleotides 617–655 of SEQ ID NO:12. Probes can be labeled to provide a detectable signal, such as with an enzyme, biotin, a radionuclide such as $^{32}P$ or $^{35}S$, fluorophore, chemiluminescer, paramagnetic particle and the like, which are commercially available from many sources, such as Molecular Probes, Inc., Eugene, Oreg., and Amersham Corp., Arlington Heights, Ill., using techniques that are well known in the art.

Zins2 nucleotide probes can also be used to detect the overexpression of post-translationally modified Zins2 polypeptide and polypeptide fragments using PCR. Gene amplification of such sequences can be determined indirectly by assay of a patient body fluid to detect the presence of elevated levels of Zins2. Suitable body fluids include serum and urine and exudates of the putative tumor tissues.

For pharmaceutical use, the polypeptides of the present invention are formulated for parenteral, particularly intravenous or subcutaneous, delivery according to conventional methods. Intravenous administration will be by bolus injection or infusion over a typical period of one to several hours. In general, pharmaceutical formulations will include a testis-specific insulin homolog polypeptide in combination with, a pharmaceutically acceptable vehicle, such as saline, buffered saline, 5% dextrose in water or the like. Formulations may further include one or more excipients, preservatives, solubilizers, buffering agents, albumin to prevent protein loss on vial surfaces, etc. Methods of formulation are well known in the art and are disclosed, for example, in *Remington's Pharmaceutical Sciences,* Gennaro, ed., Mack Publishing Co., Easton Pa., 1990, which is incorporated herein by reference. Therapeutic doses will generally be in the range of 0.1 to 100 pg/kg of patient weight per day, preferably 0.5–20 µg/kg per day, with the exact dose determined by the clinician according to accepted standards, taking into account the nature and severity of the condition to be treated, patient traits, etc. Determination of dose is within the level of ordinary skill in the art. The polypeptides may be administered for acute treatment, over one week or less, often over a period of one to three days or may be used in chronic treatment, over several months or years.

EXAMPLES

Example 1

A.
Scanning of a cDNA database for sequences structurally homologous to insulin revealed an expressed sequence tag (EST) from a human testis cDNA library that is homologous to relaxin, with the homology spanning nucleotides 1–189 of SEQ ID NO: 8. This EST encoded a secretory signal sequence followed by the insulin, family B chain motif. Analysis of the sequence revealed a putative amphipathic helix, providing additional confirmation of an insulin B chain homology.

B.
The rat first strand cDNA reaction contained 10 µl of rat testis poly d(T)-selected poly (A)+ mRNA (Clontech, Palo Alto, Calif.) at a concentration of 1.0 µg/µl, and 2 µl of 20 pmole/µl first strand primer ZC6091 (SEQ ID NO: 3) containing an Xho I restriction site. The mixture was heated at 70° C. for 4 minutes and cooled by chilling on ice. First strand cDNA synthesis was initiated by the addition of 8 µl of first strand buffer (5×SUPERSCRIPT™ buffer; Life Technologies, Gaithersburg, Md.), 4 μl of 100 mM dithiothreitol, and 2 μl of a deoxynucleotide triphosphate solution containing 10 mM each of dATP, dGTP and 5-methyl-dCTP (Pharmacia LKB Biotechnology, Piscataway, N.J.) to the RNA-primer mixture. The reaction mixture was incubated at 45° C. for 2 minutes, followed by the addition of 10 μl of 200 U/μl RNase H– reverse transcriptase (SUPERSCRIPT II®; Life Technologies). The efficiency of the first strand synthesis was analyzed in a parallel reaction by the addition of 10 μCi of $^{32}$P-αdCTP to 5 μl aliquot from one of the reaction mixtures to label the reaction for analysis. The reactions were incubated at 45° C. for 1 hour followed by an incubation at 50° C. for 10 minutes. Unincorporated $^{32}$P-αdCTP in the labeled reaction was removed by chromatography on a 400 pore size gel filtration column (Clontech). The unincorporated nucleotides and primers in the unlabeled first strand reactions were removed by chromatography on 400 pore size gel filtration column (Clontech). The length of labeled first strand cDNA was determined by agarose gel electrophoresis.

The second strand reaction contained 102 μl of the unlabeled first strand cDNA, 30 μl of 5× polymerase I buffer (125 mM Tris: HCl, pH 7.5, 500 mM KCl, 25 mM MgCl$_2$, 50 mM (NH$_4$)$_2$SO$_4$)), 2 μl of 100 mM dithiothreitol, 3 μl of a solution containing 10 mM of each deoxynucleotide triphosphate, 5 μl of 5 mM β-NAD, 2 μl of 3 U/μl E. coli DNA ligase (New England Biolabs, Inc., Beverly, Mass.), 5 μl of 10 U/μl E. coli DNA polymerase I (New England Biolabs), and 1.5 μl of 2 U/μl RNase H (Life Technologies). A 10 μl aliquot from one of the second strand synthesis reactions was labeled by the addition of 10 μCi $^{32}$P-αdCTP to monitor the efficiency of second strand synthesis. The reactions were incubated at 16° C. for two hours, followed by the addition of 10 μl T4 DNA polymerase (10 U/μl, Boehringer Mannheim, Indianapolis, Ind.) and incubated for an additional 5 minutes at 16° C. Unincorporated $^{32}$P-αdCTP in the labeled reaction was removed by chromatography through a 400 pore size gel filtration column (Clontech) before analysis by agarose gel electrophoresis. The unlabeled was terminated by the addition of 20 μl 0.5 M EDTA and extraction with phenol/chloroform and chloroform followed by ethanol precipitation in the presence of 2.5 M ammonium acetate. The yield of cDNA was estimated to be approximately 2 μg from starting mRNA template of 10 μg.

Eco RI adapters were ligated onto the 5' ends of the cDNA described above to enable cloning into an expression vector. A 10.5 μl aliquot of cDNA (~2 μg) and 5 μl of 65 pmole/μl of Eco RI adapter (Pharmacia LKB Biotechnology Inc.) were mixed with 2.5 μl 10×ligase buffer 66 mM Tris-HCl pH 7.5, 10 mM MgCl$_2$, 2.5 μl of 10 mM ATP and 1 μl of 15 U/μl T4 DNA ligase (Promega Corp., Madison, Wis.). The reaction was incubated overnight (~12 hours) at 12° C. The reaction was terminated by incubation at 70° C. for 20 minutes. After incubation, the reaction was cooled to 37° C. To the reaction was added 2.5 μl 10 mM ATP and 3 μl 10 U/μl T4 polynucleotide kinase (Life Technologies) to phosphorylate the ligated Eco RI adapters.

To facilitate the directional cloning of the cDNA into an expression vector, the cDNA was digested with Xho I, resulting in a cDNA having a 5' Eco RI cohesive end and a 3' Xho I cohesive end. The Xho I restriction site at the 3' end of the cDNA had been previously introduced using the ZC6091 primer (SEQ ID NO: 3). Restriction enzyme digestion was carried out in a reaction mixture containing 25 μl of cDNA described above, 15 μl of 10×H Buffer (Boehringer Mannheim), 109 μl H$_2$O, and 1.0 μl of 40 U/μl Xho I (Boehringer Mannheim). Digestion was carried out at 37° C. for 40 minutes. The reaction was terminated by incubation at 65° C. for 10 minutes and chromatography through a 400 pore size gel filtration column (Clontech).

The cDNA was ethanol precipitated, washed with 70% ethanol, air dried and resuspended in 20 μl of 1×gel loading buffer (10 mM Tris:HCl, pH 8.0, 1 mM EDTA, 5% glycerol and 0.125% bromphenol blue). The resuspended cDNA was heated to 65° C. for 5 minutes, cooled on ice and electrophoresed on a 0.8% low melt agarose gel. The contaminating adapters and cDNA below 0.6 Kb in length were excised from the gel. The electrodes were reversed, and the cDNA was electrophoresed until concentrated near the lane origin. The area of the gel containing the concentrated cDNA was excised and placed in a microfuge tube, and the approximate volume of the gel slice was determined. An aliquot of water approximately three times the volume of the gel slice (300 μl) and 35 μl 10×β-agarose I buffer (New England Biolabs) was added to the tube, and the agarose was melted by heating to 65° C. for 15 minutes. Following equilibration of the sample to 45° C., 3 μl of 1 U/μl β-agarose I (New England Biolabs) was added, and the mixture was incubated for 60 minutes at 45° C. to digest the agarose. After incubation, 40 μl of 3 M Na acetate was added to the sample, and the mixture was incubated on ice for 15 minutes. The sample was centrifuged at 14,000×g for 15 minutes at room temperature to remove undigested agarose. The cDNA was ethanol precipitated, washed in 70% ethanol, air-dried and resuspended in 10 μl water.

The resulting cDNA was cloned into the lambda phage vector λZap® II that was predigested with Eco RI and Xho I and dephosphorylated (Stratagene Cloning Systems, La Jolla, Calif.). Ligation of the cDNA to the λZap® II vector was carried out in a reaction mixture containing 1.0 μl of prepared vector, 1.0 μl of rat testis cDNA, 1.0 μl 10×Ligase Buffer (Promega), 1.0 μl of 10 mM ATP, 5 μl water, and 1.0 μl of T4 DNA Ligase at 15 units/ml (Promega). The ligation mixture was incubated at 5° C.–15° C. overnight in a temperature gradient. After incubation, the ligation mixture was packaged into phage using GIGPACK$^α$ III GOLD packaging extract (Stratagene Cloning Systems) and the resulting library was titered according to the manufacturer's specifications.

The rat testis λZap® II library was used to infect XLI Blue MRF' host cells (Stratagene Cloning Systems), and 2×10$^6$ pfu were plated onto 45 150-mm NZY plates. The inoculated plates were incubated overnight at 37° C. Filter plaques lifts were made using HYBOND-N nylon membranes (Amersham, Arlington Heights, Ill.), according to the procedures provided by the manufacturer. The filters were processed by denaturation in solution containing 1.5 M NaCl and 0.5 M NaOH for 7 minutes at room temperature. The filters were blotted briefly on filter paper to remove excess denaturation solution, followed by neutralization for 5 minutes in 0.5 M Tris-HCl, pH 7.2, and 1.5 M NaCl. Phage DNA was fixed onto the filters with 1,200 μJoules of UV energy in a STRATALINKER$^α$ UV Crosslinker (Stratagene Cloning Systems). After fixing, the filters were prehybridized in hybridization solution (5×SSC, 5×Denhardt's solution, 0.2% SDS and 1 mM EDTA). Heat denatured, sheared salmon sperm DNA at a final concentration of 100 μg/ml was added. The filters were prehybridized at 65° C. overnight.

A probe was prepared as a PCR product by using oligonucleotide primers designed to amplify the human testis-specific insulin homolog cDNA coding region (see Example 5). A PCP reaction mixture containing 2 µl of ZC10008 (SEQ ID NO: 4) and 2 µl of ZC10491 (SEQ ID NO: 5), 1 µl of 100 fentogram pSLHIT-10 (described in Example 5), 1 µl of 10 mM dNTPs, 10 µl of 10×KlenTaq buffer (Clontech), 82 µl water, and 2 µl KlenTaq DNA polymerase (Clontech). The PCR reaction was run as follows: 1 cycle at 94° C. for 1 minute; 30 cycles at 95° C. for 20 seconds, 60° C. for 20 seconds, 68° C. for 1 minute; and 1 cycle at 68° C. for 10 minutes. The PCR product was gel purified on a 1.5% low melt agarose gel.

Fifty nanograms PCR product was radiolabeled with $^{32}$P dCTP by random priming using the MEGAPRIME™ DNA Labeling System (Amersham), according to the manufacturer's specifications. The prehybridization solution was replaced with fresh hybridization solution containing 1.4× $10^6$ cpm/ml labeled probe and allowed to hybridize for 64 hours at 60° C. After hybridization, the hybridization solution was removed and the filters were rinsed in a wash solution containing 1×SSC, 0.25% SDS and 1 mM EDTA at 45° C. The filters were placed on autoradiograph film and exposed at −70° C. with intensifying screens for 96 hours.

Examination of the autoradiographs revealed 134 regions that hybridized with the labeled probe. Agar plugs were picked from 73 regions for purification. Each agar plug was soaked overnight in 1 ml of SM containing 1% (v/v) chloroform (Sambrook et al. *Molecular Cloning: A Laboratory Manual*, 2nd ed., Cold Spring Harbor Laboratory Press, Cold Spring Harbor, N.Y., 1989). After incubation, the phage from each plug were diluted 1:1000 in SM. Aliquots of 12.5 µl were plated on *E. coli* XL-1 Blue MRF' cells. The plates were incubated overnight at 37° C., and filter lifts were prepared, prehybridized, hybridized, washed and autoradiographed as described above. Examination of the resulting autoradiographs revealed positive signals on 3 filter lifts.

The plasmids were excised using an ExASSIST/SOLR™ system (Stratagene Cloning Systems), according to the manufacturer's specification. These plasmids were amplified by PCR for insert size determination and sequencing. A clone, designated pSLRatzins2-1, was shown to have a 0.79 kb insert and contained the sequence shown in SEQ ID NO: 1.

Example 2

A probe was prepared from the full length coding sequence of zins2 and used to probe Human Multiple Tissue Northern Blots (Clontech). The Northern analysis revealed a band at approximately 1.2 kb that was only present in testis.

Example 3

In situ hybridization was done to localize expression of Zins2 polypeptide within the testis.

A.

Oligonucleotide primers were designed to begin priming at the ATG and introduce a Sal I cloning site (ZC10008; SEQ ID NO:4; and ZC10491; SEQ ID NO:5), designed to begin priming immediately downstream from the termination codon sequence, eliminating the 3' non-coding region and introducing a Xba I cloning site. Template for the PCR was testis cDNA and the reaction was done as follows: 1 µl template DNA; 10 µl KlenTaq buffer (Clontech); 1 µl of 10 mM dNTPs; 2 µl of each ZC10008 (SEQ ID NO: 4) and ZC10491 (SEQ ID NO: 5); 87 µl of H$_2$O and 1 µl of KlenTaq Polymerase (Clontech) were mixed and run for 20 cycles at 95° C. for 30 seconds, 60° C. for 30 seconds and 68° C. for 2 minutes. The resulting PCR product was phenol-chloroform extracted and DNA was precipitated with ethanol and resuspended. The resuspended DNA was digested with Sal I and Xba I and ligated into pBluescript SK$^+$® phagemid vector (Stratagene).

An antisense riboprobe was prepared utilizing the T7 polymerase promoter of the vector. 30 µl of pSLHIT-7 was digested with 150 units of Xba I and phenol-chloroform extracted, precipitated in ethanol and resuspended in water. A sense riboprobe was prepared utilizing the T3 polymerase promoter by digesting 30 µl of pSLHIT-7 with 200 units of Xho I, and then phenol-chloroform extracted, precipitated in ethanol and resuspended in water.

Labeling of the DNA was done in the following reaction: 1 µg of DNA in a 20 µl volume of water, 2 µl of 10×transcription buffer (Ambion, Austin, Tex.) ; 1 µl of 10 mM each, ATP, CTP, and GTP; 5 µl $^{35}$S UTP at 1000 Ci/mmol at 12,500 mCi/ml (Amersham) and 2 µl T3 or T7 polymerase (Ambion) were mixed and incubated at 37° C. for 1 hour. After incubation, the reactions were centrifuged and 50 µl of SET-DTT (100 µl 10% SDS; 10 µl of 1 M Tris, pH 7.5; 2 µl of 0.5 M EDTA, pH 8.0; 10 µl of 1 M DTT; 878 µl of water) was added to each tube and the reactions were incubated at 65° C. for 5 min. The reaction mixtures were centrifuged and 1 µl/reaction was analyzed for cpm. The remaining (69 µl) of the reaction was purified over a Sephadex G-50 spin column (Pharmacia). The resulting probes were 1.8×$10^6$ cpm/µl for the antisense probe and 8.9×$10^6$ cpm/µl for the sense probe.

B.

Testis tissue was prepared for in situ hybridization using techniques known in the art. See, for example, Simmons et al., *J. of Histotechnology* 12:169–181, 1989; and Sylvester et al., *Biol. of Reproduction* 45:195–207, 1991.

Briefly, Macaque monkey testicular tissue was prepared as follows:

Twenty minutes prior to perfusion with saline and fixatives, the monkey was perfused with heparin.

Tubing was primed with saline (9% NaCl) and fixatives (see Tables 3 and 4), with fixatives held on ice and saline at room temperature.

TABLE 3

| Fix A | 50 ml |
| --- | --- |
| NaOH | 0.20 g |
| paraformaldehyde | 2 g |
| NaAcetate, trihydrate | 1.13 g |
| Adjust pH to 6.5 and use at 4° C. | |

TABLE 4

| Fix B | 50 ml |
| --- | --- |
| NaOH | 0.2 g |
| paraformaldehyde | 2 g |
| Na Tetraborate-10 H$_2$O | 1.91 |
| Adjust the pH to 9.5 and store at 4° C. | |
| Fix C with 10% sucrose | |
| Place 2 g of sucrose in a 50 ml conical centrifuge tube, then add fix B to 20 ml. | |

At time zero, the monkey was injected with sodium pentobarbitol, and when the animal no longer responded to pinching of the foot pad, the surgical procedure was begun.

The chest cavity opened to the diaphragm to clear the working field. A blunted 18 g needle (attached to tubing filled with saline) was inserted into the left ventricle. Once the heart swelled the right atrium was clipped. The pump setting to was adjusted gradually to a rate of 40 ml/min.

The testes were exposed, watching for the bleaching of the testicular artery and testicular vein, an indication that blood is being replaced by saline.

After the testes were bleached, the pump was switched from saline over to Fix A. Muscle twitching or contraction was used as an indication that fixing had begun. 250 ml Fix A at 40 ml/min was perfused into the animal. After perfusion with Fix A was completed, the pump was switched to Fix B for 5 minutes at 40 ml/min, and then reduced to a rate of 20 ml/min until 400–450 ml Fix B was perfused.

The testes were excised and stored in Fix C, overnight at 4° C.

C.

Slides of cross sections of Macaque testes were prepared for hybridization as follows:

The slides were deparaffinized by immersing in xylene 2 times, 10 min. After deparaffinizing, the slides were rehydrated by immersing in decreasing concentrations of ethanol solutions (100%, 99%, 95%, 85%, 70%, 50%, 30%) for 2 minutes each.

The slides were treated with pre-heated Proteinase K solution (20 µl 20 mg/ml Proteinase K, 40 ml of 0.5 M EDTA, pH 8.0, 320 ml sterile $H_2O$) at 37° C. for 30 minutes. The slides were rinsed in sterile $H_2O$, 2 min. and then slides were rinsed in 0.1 M triethanolamine, pH 8.0, 3 min. The slides were rinsed in acetylation solution (500 µl acetic anhydride, 200 ml of 0.1 M Triethanolamine), 10 min. The slides were rinsed twice, 2 min in 2×SSC.

The tissue was dehydrated by immersing slides in increasing concentrations of ethanol solutions (in the reverse order to the listed above) and then dried under vacuum with desiccant for 1½ hours.

D.

Prepared Macaque testis slides were hybridized in a solution containing: 2.5 ml of 100% deionized formamide (50%), 10% dextran sulfate, 3 M NaCl, 1×Denhardt's solution, 100 mM Tris, pH 8.0, 20 µl of 10 mg/ml salmon sperm DNA (40 ug/ml), and 100 mM DTT. Probes (as described in Example 3A) were added for a final volume of radioactivity of $1.67×10^7$ cpm/ml.

70 µl total probe was added (approximately $1.2×10^6$ cpm/slide) and overlayed each glide with parafilm. The slides were hybridized overnight at 50° C. in a moist slide chamber.

E.

After incubation, slides were placed in 4×SSC for about 30 minutes to loosen parafilm.

The parafilm was removed, and the slides were washed in 4×SSC 3 times, 5 minutes each, and then treated with RNase solution (20 µg RNase A, 0.5 M NaCl, 10 mM Tris:HCl pH 8.0, 1 mM EDTA pH 8.0).

The RNase solution was preheated to 37° C. and slides were incubated in the RNase solution for 30 minutes at 37° C. After incubation, the slides were washed twice in 2×SSC/10 mM DTT for 10 minutes each at RT, once in 1×SSC/10 mM DTT for 10 minutes at RT, and once in 0.5×SSC/10 mM DTT for 10 minutes at RT. The slides were washed for 30 minutes at 60–65° C. in preheated 0.1×SSC/10 mM DTT.

The tissue samples were dehydrated using ethanol solutions series of 30%, 50%, 70%, 85%, 95%, 99%, and 100%. After dehydration, the slides were drained well and place under vacuum with desiccant for 1 hour.

F.

Slides were treated with photographic emulsion by dipping pre-warmed (40° C.) slides into melted (42° C.) Kodak NTB2 Emulsion (Kodak, Rochester, N.Y.), allowing slides to dry, then storing them in light-tight, sealed containers with desiccant at 4° C.

Slides were developed at several intervals following emulsion by warming to room temperature, immersing in full strength Kodak D-19 developer (Kodak), rinsing 8 times in water, immersing 10 min. in Kodak fixer (Kodak), and dipping in water 8 times.

Slides were stained as follows:

1½ min. in hematoxylin solution, 5 min. in sterile water, 5 brief rinses in 95% ethanol, 1 min. in 0.1 Eosin Y, 2 min in sterile water, 8 brief rinses in 95% ethanol, 2 min. in 95% ethanol, 8 brief rinses in 100% ethanol, 2 min. in 100% ethanol, 8 brief rinses in xylene, 2 min. in xylene.

Slides were re-dipped in xylene then overlayed with a small amount of Permount (Fisher SP15-100) and covered with coverslips and viewed under microscope for silver grains showing distribution of zins2 (with anti-sense probe) vs. negative control (sense probe). Zins2 mRNA was found by in situ hybridization to be localized in the seminiferous tubules and epidymus.

Example 4

Zins2 was mapped to human chromosome 9 by PCR using the Human/Rodent Somatic Cell Hybrid Mapping Panel Number 2 (National Institute of General Medical Sciences, Coriell Institute of Medical Research, Camden, N.J.). The panel consists of DNA isolated from 24 human/rodent somatic cell hybrids each retaining one specific human chromosome and the parental DNAs. Specific Zins2 oligonucleotide primers, sense, ZC10684, (SEQ ID NO: 6), and antisense, ZC10685, (SEQ ID NO: 7), were used for PCR amplification. PCR conditions were as follows: an initial 1 cycle 5 minute denaturation at 95° C., 35 cycles of a 30 second denaturation at 95° C., 2 minute annealing at 68° C. and 30 second extension at 72° C., followed by a final 1 cycle extension of 8 minutes at 72° C. Each 50 µl PCR reaction consisted of 5 µl 10×KlenTaq PCR reaction buffer (CLONTECH Laboratories, Inc., Palo Alto, Calif.), 4 µl dNTPs mix (2.5 mM each, PERKIN-ELMER, Foster City, Calif.), 2.5 µl of (20 picomole/µl) ZC10684 (SEQ ID NO: 6) 2.5 µl of (20 picomole/µl) ZC10685 (SEQ ID NO: 7), 25 µl PCR-grade ddH20, 1 µl 50×Advantage KlenTaq Polymerase Mix (CLONTECH Laboratories, Inc.), and 10 µl DNA from the respective human/rodent somatic cell hybrid (10 ng/µl). The reactions were separated by electrophoresis on a 3% NuSieve GTG agarose gel (FMC Bioproducts, Rockland, Me.). The results demonstrated that Zins2 mapped to human chromosome 9.

Zins2 was further mapped to chromosome 9p24 using the commercially available version of the Whitehead Institute/MIT Center for Genome Research's GeneBridge 4 Radiation Hybrid Panel (Research Genetics, Inc., Huntsville, Ala.). The GeneBridge 4 Radiation Hybrid Panel contains PCRable DNAs from each of 93 radiation hybrid clones, plus two control DNAs (the HFL donor and the A23 recipient). A publicly available WWW server (http://www-genome.wi.mit.edu/cgi-bin/contig/rhmapper.pl) allows mapping relative to the Whitehead Institute/MIT Center for Genome Research's radiation hybrid map of the human genome (the "WICGR" radiation hybrid map) which was constructed with the GeneBridge 4 Radiation Hybrid Panel.

For the mapping of Zins2 with the GeneBridge 4 RH Panel, 25 µl reactions were set up in a PCRable 96-well microtiter plate (Stratagene, La Jolla, Calif.) and used in a RoboCycler Gradient 96 thermal cycler (Stratagene). Each of the 95 PCR reactions consisted of 2.5 µl 10×KlenTaq reaction buffer (Clontech), 2 µl dNTPs mix (2.5 mM each, Perkin-Elmer, Foster City, Calif.), 1.25 µl sense primer, ZC 10,684 (SEQ ID NO:6), 1.25 µl antisense primer, ZC 10,685 (SEQ ID NO:7), 2.5 µl RediLoad (Research Genetics), 0.5 µl 50×Advantage KlenTaq Polymerase Mix (Clontech), 25 ng of DNA from an individual hybrid clone or control and ddH$_2$O for a total volume of 25 µl. The reactions were overlaid with an equal amount of mineral oil and sealed. The PCR cycler conditions were as follows: an initial 1 cycle 5 minute denaturation at 95° C., 35 cycles of a 1 minute denaturation at 95° C., 1 minute annealing at 70° C. and 1 minute extension at 72° C., followed by a final 1 cycle extension of 7 minutes at 72° C. The reactions were separated by electrophoresis on a 3% NuSieve GTG agarose gel (FMC Bioproducts, Rockland, Me.).

The results showed that Zins2 maps 13.70 cR_3000 from the top of the human chromosome 9 linkage group on the WICGR radiation hybrid map. Proximal and distal framework makers were CHLC.GCT3G05 and D9S178, respectively. The use of surrounding markers positions Zins2 in the 9p24 region on the integrated LDB chromosome 9 map (The Genetic Location Database, University of Southampton, WWW server: http://cedar.genetics.soton.ac.uk/public_html/).

Example 5

Oligonucleotide primers were designed to begin priming at the putative start codon of the EST sequence and included sequence to encode a Kozak translational consensus sequence upstream of the start codon and a Sal I cloning site. The template for the PCR was Marathon Ready human testis cDNA (Clontech, Palo Alto, Calif.). The conditions for the PCR were as follows: 5 µl template cDNA; 10 µl KlenTaq 10×buffer; 1 µl 10 mM dNTPs; 1 µl of 20 pmole/µl ZC1000 (SEQ ID NO: 4); 2 µl of 10 pmole/µl AP-1 primer (Clontech); 79 µl H$_2$O and 2 µl KlenTaq polymerase. The reaction was run for 30 cycles at 95° C. for 30 seconds and 68° C. for 2 minutes.

The amplified DNA was gel purified in low melt agarose and a 700 base pair band was seen. Sequence analysis of the band determined that the PCR product duplicated the EST sequence and that the cDNA sequence was a full-length sequence with a 202 base pair 3' untranslated sequence as shown in SEQ ID NO: 8. The cDNA was designated Zins2. The PCR product was digested with Sal I and Eco RI and ligated with the Sal I and Eco RI digested expression vector pHz-200.

pHZ-200 is the same as pHZ-1 with the exception that the dihydrofolate reductase sequence was substituted for the neomycin resistance gene. Plasmid pHZ-1 is an expression vector that may be used to express protein in mammalian cells or in a frog oocyte translation system from mRNAs that have been transcribed in vitro. The pHZ-1 expression unit comprises the mouse metallothionein-1 promoter, the bacteriophage T7 promoter flanked by multiple cloning banks containing unique restriction sites for insertion of coding sequences, the human growth hormone terminator and the bacteriophage T7 terminator. In addition, pHZ-1 contains an E. coli origin of replication; a bacterial beta lactamase gene; a mammalian selectable marker expression unit comprising the SV40 promoter and origin, a neomycin resistance gene and the SV40 transcription terminator. The plasmids resulting from the ligation reaction were designated pSLHIT-1, 2, 3, and 4.

Oligonucleotide primers were designed to hybridize to the 5' and 3' ends of the coding region of Zins2 (ZC10009, SEQ ID NO: 9 and ZC10537, SEQ ID NO: 10). Using a human testis cDNA library as template, PCR was performed as follows: parallel reaction mixtures containing 1 µl template DNA (25 ng), 2 µl of 20 pmole/µl ZC100009 (SEQ ID NO: 9) and ZC10537 (SEQ ID NO: 10), 1 µl of 10 mM dNTPs, 1 µl of 2.5 u/µl Native Pfu polymerase (Stratagene), 10 µl of 10×native Pfu buffer (Stratagene) were combined. The reaction was run for 25 cycles at 95° C. for 30 seconds, 55° C. or 50° C. for 30 seconds, 72° C. for 1 minute and followed by a 5 minute incubation at 72° C. The PCR products from the parallel reactions were gel purified and pooled.

The pooled PCR products were diluted 1:10 and 1:100 and used as template for another PCR reaction, where oligonucleotides were designed to incorporate restriction sites at the 5' and 3' ends of the Zins2 coding region. The reaction mixture contained 1 µl of either 1:10 or 1:100 template, 2 µl of 20 pmole/µl of each ZC10008 (SEQ ID NO: 4) or ZC10538 (SEQ ID NO: 11), 1 µl of 10 mM dNTPs, 10 µl of 10×Native Pfu Buffer (Stratagene), 1 µl of 2.5 u/µl Native Pfu polymerase (Stratagene) and 83 µl water were combined. The reaction was run for 3 cycles at 95° C. for 30 seconds, 40° C. for 30 seconds, 72° C. for 1 minute; 20 cycles at 95° C. for 30 seconds, 47° C. for 30 seconds, 72° C. for 1 minute; followed by a 5 minute incubation at 72° C.

The PCR products were pooled and digested with Proteinase K, phenol-chloroform extracted, ethanol precipitated and resuspended in water. The PCR products were gel purified on 10% low melt agarose. The DNA was digested with Sal I and Eco RI and ligated in Sal I/Eco RI digested pHZ-200. The resulting plasmid was designated pSLHIT-10 and was sequence analyzed.

Example 6

A full-length human Zins2 cDNA was obtained by screening a λZAP® II human testis cDNA. The construction of the testis cDNA library was as follows: The first strand cDNA reaction contained 15 µl of human testis twice poly d(T)-selected poly (A)$^+$ mRNA (Clontech) at a concentration of 1.0 µg/µl, and 3 µl of 20 pmole/µl first strand primer ZC6091 (SEQ ID NO: 3) containing an Xho I restriction site. The mixture was heated at 70° C. for 4 minutes and cooled by chilling on ice. First strand cDNA synthesis was initiated by the addition of 12 µl of first strand buffer (5×SUPERSCRIPT™ buffer; Life Technologies, Gaithersburg, Md.), 6 µl of 100 mM dithiothreitol, and 3 µl of a deoxynucleotide triphosphate solution containing 10 mM each of dTTP, DATP, dGTP and 5-methyl-dCTP (Pharmacia LKB Biotechnology, Piscataway, N.J.) to the RNA-primer mixture. The reaction mixture was incubated at 37° C. for 2 minutes, followed by the addition of 15 µl of 200 U/µl RNase H$^-$ reverse transcriptase (SUPERSCRIPT II®; Life Technologies). The efficiency of the first strand synthesis was analyzed in a parallel reaction by the addition of 5 µCi of $^{32}$P-αdCTP to 5 µl aliquot from one of the reaction mixtures to label the reaction for analysis. The reactions were incubated at 37° C. for 10 minutes, 45° C. for 1 hour, then incubated at 50° C. for 10 minutes. Unincorporated 32P-αdCTP in the labeled reaction was removed by chromatography on a 400 pore size gel filtration column (Clontech Laboratories). The unincorporated nucleotides and primers in the unlabeled first strand reactions were removed by chromatography on 400 pore size gel filtration column (Clontech). The length of labeled first strand cDNA was determined by agarose gel electrophoresis.

The second strand reaction contained 120 µl of the unlabeled first strand CDNA, 36 µl of 5×polymerase I buffer (125 mM Tris: HCl, pH 7.5, 500 mM KCl, 25 mM $MgCl_2$, 50 mM $(NH_4)_2SO_4$)), 2.4 µl of 100 mM dithiothreitol, 3.6 µl of a solution containing 10 mM of each deoxynucleotide triphosphate, 6 µl of 5 mM β-NAD, 3.6 µl of 3 U/µl E. coli DNA ligase (New England Biolabs; Beverly, Mass.), 9 µl of 10 U/µl E. coli DNA polymerase I (New England Biolabs), and 1.8 µl of 2 U/µl RNase H (Life Technologies). A 10 µl aliquot from one of the second strand synthesis reactions was labeled by the addition of 10 µCi $^{32}$P-αdCTP to monitor the efficiency of second strand synthesis. The reactions were incubated at 16° C. for two hours, followed by the addition of 15 µl T4 DNA polymerase (10 U/µl, Boehringer Mannheim, Indianapolis, Ind.) and incubated for an additional 5 minutes at 16° C. Unincorporated $^{32}$P-αdCTP in the labeled reaction was removed by chromatography through a 400 pore size gel filtration column (Clontech) before analysis by agarose gel electrophoresis. The unlabeled was terminated by the addition of 20 µl 0.5 M EDTA and extraction with phenol/chloroform and chloroform followed by ethanol precipitation in the presence of 2.5 M ammonium acetate and 4 µg of glycogen carrier. The yield of cDNA was estimated to be approximately 3 µg from starting mRNA template of 15 µg.

Eco RI adapters were ligated onto the 5' ends of the cDNA described above to enable cloning into an expression vector. A 10 µl aliquot of cDNA (~1.5 µg) and 5 µl of 65 pmole/µl of Eco RI adapter (Pharmacia LKB Biotechnology Inc.) were mixed with 2 µl 10×ligase buffer (660 mM Tris-HCl pH 7.5, 100 mM $MgCl_2$), 2 µl of 10 mM ATP and 1 µl of is U/µl T4 DNA ligase (Promega Corp., Madison, Wis.). The reaction was incubated 2 hours at 5° C., two hours at 7.5° C., 2 hours at 10° C., and 10 hours at 12.5° C. The reaction was terminated by incubation at 70° C. for 20 minutes.

To facilitate the directional cloning of the cDNA into an expression vector, the cDNA was digested with Xho I, resulting in a cDNA having a 5' Eco RI cohesive end and a 3' Xho I cohesive end. The Xho I restriction site at the 3' end of the cDNA had been previously introduced using the ZC6091 primer (SEQ ID NO: 3). Restriction enzyme digestion was carried out in a reaction mixture containing 20 µl of cDNA described above, 10 µl of 10×H Buffer. (Boehringer Mannheim), 69 µl $H_2O$, and 1.0 µl of 40 U/µl Xho I (Boehringer Mannheim). Digestion was carried out at 37° C. for 40 minutes. The reaction was terminated by incubation at 70° C. for 10 minutes and chromatography through a 400 pore size gel filtration column (Clontech Laboratories).

The cDNA was ethanol precipitated, washed with 70% ethanol, air dried and resuspended in 14 µl water, 2 µl of ligase buffer (Promega Corp., Madison Wis.), 2 µl T4 polynucleotide kinase (10 U/µl, Life Technologies). Following incubation at 37° C. for 30 minutes, the cDNA was heated to 65° C. for 5 minutes, cooled on ice, and electrophoresed on a 0.8% low melt agarose gel. The contaminating adapters and cDNA below 0.6 Kb in length were excised from the gel. The electrodes were reversed, and the cDNA was electrophoresed until concentrated near the lane origin. The area of the gel containing the concentrated cDNA was excised and placed in a microfuge tube, and the approximate volume of the gel slice was determined. An aliquot of water approximately three times the volume of the gel slice (300 µl) and 35 µl 10×β-agarose I buffer (New England Biolabs) was added to the tube, and the agarose was melted by heating to 65° C. for 15 minutes. Following equilibration of the sample to 45° C., 3 µl of 1 U/µl β-agarose I (New England Biolabs) was added, and the mixture was incubated for 60 minutes at 45° C. to digest the agarose. After incubation, 40 µl of 3 M Na acetate was added to the sample, and the mixture was incubated on ice for 15 minutes. The sample was centrifuged at 14,000×g for 15 minutes at room temperature to remove undigested agarose. The cDNA was ethanol precipitated, washed in 70% ethanol, air-dried and resuspended in 10 µl water.

The resulting cDNA was cloned into the lambda phage vector λZap® II (Stratagene Cloning Systems) that was predigested with Eco RI and Xho I and dephosphorylated. Ligation of the cDNA to the λZap® II vector was carried out in a reaction mixture containing 1.0 µl of prepared vector, 1.0 µl of human testis cDNA, 1.0 µl 10×Ligase Buffer (Promega Corp.), 1.0 µl of 10 mM ATP, 5 µl water, and 1.0 µl of T4 DNA Ligase at 15 units/ml (Promega Corp.). The ligation mixture was incubated at 5° C.–15° C. overnight in a temperature gradient. After incubation, the ligation mixture was packaged into phage using an in vitro packaging extract (Gigapack® III Gold packaging extract; Stratagene Cloning Systems), and the resulting library was titered according to the manufacturer's specifications.

The human testis λZap® II library was used to infect E. coli host cells (XL1-Blue MRF' strain; Stratagene Cloning Systems), and 1.5×10$^6$ pfu were plated onto 150-mm NZY plates at a density of ~40,000 pfu/plate. The inoculated plates were incubated overnight at 37° C. Filter plaques lifts were made using nylon membranes (Hybond™-N; Amersham), according to the procedures provided by the manufacturer. The filters were processed by denaturation in solution containing 1.5 M NaCl and 0.5 M NaOH for 7 minutes at room temperature. The filters were blotted briefly on filter paper to remove excess denaturation solution, followed by neutralization for 5 minutes in 1 M Tris-HCl, pH 7.5, and 1.5 M NaCl. Phage DNA was fixed onto the filters with 1,200 µJoules of UV energy in a UV Crosslinker (Stratalinker®; Stratagene Cloning Systems). After fixing, the filters were prehybridized in hybridization solution (5×SSC, 5×Denhardt's solution, 0.2% SDS and 1 mM EDTA). Heat denatured, sheared salmon sperm DNA at a final concentration of 100 µg/ml was added. The filters were prehybridized at 65° C. overnight.

A probe was prepared as a PCR product by using oligonucleotide primers designed to amplify the human testis-specific insulin homolog cDNA coding corresponding to nucleotide 8 to nucleotide 568 of SEQ ID NO: 12. A PCR reaction mixture containing 2 µl of ZC10008 (SEQ ID NO: 4) and 2 µl of ZC10491 (SEQ ID NO: 5), 1 µl of 100 fentogram pSLHIT-10 (described in Example 5), 1 µl of 10 mM dNTPs, 10 µl of 10×KlenTaq buffer (Clontech), 82 µl water, and 2 µl KlenTaq DNA polymerase (Clontech). The PCR reaction was run as follows: 1 cycle at 94° C. for 1 minute; 30 cycles at 95° C. for 20 seconds, 60° C. for 20 seconds, 68° C. for 1 minute; and 1 cycle at 68° C. for 10 minutes. The PCR product was gel purified on a 1.5% low melt agarose gel.

Fifty nanograms PCR product was radiolabeled with $^{32}$Pα-dCTP by random priming using the MEGAPRIME™ DNA Labeling System (Amersham), according to the manufacturer's specifications. The prehybridization solution was replaced with fresh hybridization solution containing 1.4× 10$^6$ cpm/ml labeled probe and allowed to hybridize for 64 hours at 60° C. After hybridization, the hybridization solution was removed and the filters were rinsed in a wash solution containing 0.25%×SSC, 0.25% SDS and 1 mM EDTA at 65° C. The filters were placed on autoradiograph film and exposed at −70° C. with intensifying screens for 96 hours.

Examination of the autoradiographs revealed 35 regions that hybridized with the labeled probe. Agar plugs were picked from 35 regions for purification. Each agar plug was soaked overnight in 1 ml of SM containing 1% (v/v) chloroform (Sambrook et al. *Molecular Cloning: A Laboratory Manual*, 2nd ed., Cold Spring Harbor Laboratory Press, Cold Spring Harbor, N.Y., 1989). After incubation, the phage from each plug were diluted 1:1000 in SM. Aliquots of 12.5 µl were plated on *E. coli* XL-1 Blue MRF' cells. The plates were incubated overnight at 37° C., and filter lifts were prepared, prehybridized, hybridized, washed and autoradiographed as described above. Examination of the resulting autoradiographs revealed positive signals on 3 filter lifts.

The plasmids were excised using an ExASSIST/SOLR™ system (Stratagene Cloning Systems), according to the manufacturer's specification. These plasmids were amplified by PCR for insert size determination and sequencing. A clone, designated pSLZpin2, was shown to be an insert of 717 bp and contained the sequence shown in SEQ ID NO: 12.

Example 7

Additional Northern Blot analysis was carried out on a rat testis tissue blot. The blot was prepared using mRNA from whole testis taken from 20, 25, 30, 40, 52 and 67 day old Sprague-Dawley rats. Total RNAs were isolated by the single step liquid phase separation method ("Single-Step RNA Isolation form Cultured Cells or Tissues", *Current Protocols in Molecular Biolocy*, John Wiley and Son, 4.2.1–4.2.2, 1996). Ten micrograms of total RNA from each sample was separated out in a 1.2% agarose gel in 1% formaldehyde and MOPS buffer. The RNAs were transferred, overnight, onto nylon membrane (Hybond N+, Amersham Pharmacia Biotech, Inc., Piscataway, N.J.) in 10×SSC. The RNAs were then crosslinked to the membrane using a UV Stratalinker 1800 (Stratagene, La Jolla, Calif.) at 120 mJoules according to manufacturer's instruction.

Fifty microliters of the full length coding sequence of rat zins2 (Eco RI-Xho I restriction digest of the plasmid described above in Example 1) was radioactively labeled using a RADprime DNA labeling system (GIBCO BRL, Gaithersburg, Md.) according to the manufacturer's instruction. The probe was purified using a ProbeQuant G50 column (Amersham). The blot was prehybridized for 90 minutes at 65° C. Prehybridization and hybridizing solution were the same, 1% BSA, 7% SDS and 0.5 M Na Phosphate. The labeled probe was added, $2 \times 10^6$ cpm/ml and. hybridization took place overnight at 65° C. The blot was washed copiously in 0.2×SSC, 0.1% SDS at room temperature, then at 65° C. in 0.1×SSC, 0.1% SDS, followed by a final wash in 0.1×SSC, 0.1% SDS at 68° C. and exposed to a phosphoimager screen overnight and developed the following day. A 0.8 kb transcript corresponding to zins2 was seen in each of the tissue samples. The signal was weak at day 20 and grew stronger with increasing age.

A second testis development blot was prepared using mRNA from whole testis taken from 0, 10, 20, 25, 30, 40, 52, 67 and 90 day old Sprague-Dawley rats as described above. A faint signal was detected in 25 day old testis tissue with strong expression seen from day 30 to 90.

Additional Northern Blot analysis was carried out on a rat whole organ tissue blot. The blot was prepared using RNA from 20 day old rat liver, heart, kidney, lung, brain, skeletal muscle and testis tissue and 12 month old rat testis, ovary and epididymis tissue. Total RNAs were isolated and blots prepared and probed as described above for the testis Northern Blot. A 0.8 kb transcript corresponding to zins2 was seen only in 12 month old testis. Lack of signal in the 20 day testis may be due to weak signal.

A second rat whole organ tissue blot was prepared as described above from 67 day old Sprague-Dawley rat brain, kidney, liver, spleen, testis, lung, skeletal muscle, heart and pancreas. A strong signal was detected in testis and unlike in the human blot, two major species were detected at approximately 1.2 and 1.9 kb. Several minor species were detected as well. A weak signal was detected in skeletal muscle that may represent an artifact.

A second reproductive tissue blot was prepared as described above from 90 day old rat epididymis, prostate, testis, uterus and ovary. Again a strong signal in testis tissue and two bands, 1.2 and 1.9 kb were seen. There was weak expression in prostate and no expression in any other tissue.

Example 8

In situ hybridization

A rat Zins2 cDNA probe, corresponding to a region in the 5' UTR and coding regions, was generated by digesting the Bluescript plasmid containing the full length rat Zins2 cDNA, as described above, with Bst X I and Bsm I (Life Sciences). The resulting 3' overhangs were cut back by treatment with T4 Polymerase (Life Sciences) using a dNTP concentration of 100 uM. The plasmid was re-ligated using T4 ligase (Life Sciences), transformed, and screened using Sst I (Life Sciences) and Kpn I (Life Sciences). Clones yielding a an insert of approximately 320 bp were selected. One clone (5-2R) was chosen and linearized with either Sst I (antisense) or Kpn I (sense).

Antisense and sense $^{33}$P-labeled probes were generated from the template using T3 or T7 polymerase (Stratagene) as follows: 20 ng of linearized DNA, 0.6 µl of 1M DTT, 3 µl of rNTPs mixed 1:1:1 from 10 mM stocks or CTP, ATP and GTP, 4 µl of 5×Transcription Buffer (Stratagene), 9.9 µl of $^{33}$P-UTP (NEN, Boston, Mass.), 1 µl (20 units) of RNAse inhibitor (Life Technologies, Grand Island, N.Y.) and 1 µl of T3 or T7 RNA polymerase. The mixture was incubated for 1 hour at 37° C. One microliter (1 unit) of DNase free RNase was added and incubated at 37° C. for 10 minutes. Thirty microliters of DEPC water was added and the mixture was centrifuged through a G50 spin column (Amersham Pharmacia Biotech, Inc., Piscataway, N.J.). One microliter of the mixture was counted on a scintillation counter. $1 \times 10^6$ counts were run on an agarose gel which was dried and exposed to film to ensure that full length transcripts had been produced.

Ten micron sections were cut from paraffin-embedded 90 day old rat testes and mounted on to slides. Immediately prior to hybridization sections were treated twice with xylene for 10 min each and rehydrated through a series of graded ethanols [1–2 minutes each in 100% (twice), 95%, 85%, 60%, 30%] and rinsed in PBS twice for 5 minutes each. The slides were treated with 20 µg/ml proteinase K (Boehringer Mannheim, Indianapolis, Ind.) in PBS for 7 minutes at room temperature, rinsed in PBS twice for 5 minutes each and rinsed in DEPC water for approximately 30 seconds. The slides were then acetylated for 10 minutes at room temperature in 0.25% acetic anhydride in 0.1 M triethanolamine, pH 8.0. The slides were rinsed in DEPC water for approximately 30 seconds and rehydrated through a series of graded ethanols.

Sections were hybridized in a humidified chamber overnight at 55° C. in a buffer containing 50% formamide (Life Technologies), 10% dextran sulfate (Sigma Chemical Co., St. Louis, Mo.), 0.3 M NaCl, 20 mM Tris, pH 7.5, 10 mM DTT, 5 mM EDTA, 1×Denhardts solution (Sigma) and 0.4 mg/ml yeast tRNA (Life Technologies). The hybridization mixture was 90% of the above buffer and 10% probe ($2\times10^6$ cpm/cm$^2$) in DEPC water. Prior to hybridization the probe and buffer were mixed and heated at 80° C. for 2 minutes and cooled on ice for 2 minutes.

Slides were washed as follows: 5×SSC (1×SSC=0.15 M NaCl and 0.015 M sodium citrate) and 1 mM DTT at 55° C. for 20 minutes; 50% formamide, 2×SSC, and 1 mM DTT at 70° C. for 30 min; 10 mM Tris, pH 7.5, 0.5 M NaCl, and 5 mM EDTA (TNE Buffer) at 37° C. three times for 10 min each; TNE buffer containing 20 μg/ml RNase A (Life Technologies) at 37° C. for 30 min; TNE buffer at 37° C. for 15 minutes; 50% formamide, 2×SSC at 70° C. for 30 minutes; 2×SSC at 37° C. for 15 minutes; 0.1×SSC at 37° C. for 15 minutes. Slides were dehydrated through a series of graded ethanols with 0.3 M ammonium acetate up to 95% ethanol followed by 2 washes in 100% ethanol. Slides were allowed to air dry prior to dipping in Kodak emulsion NTB-2. Slides were exposed for 2 days at room temperature and developed in Kodak D-19 and fixed in Kodak Fixer. The sections were counterstained lightly with hematoxylin and eosin and mounted with a xylene based mounting medium.

The signal strength varies considerably among different seminiferous tubules suggesting that zins2 expression is regulated during sperm development in the seminiferous epithelium. Zins2 was not found in interstitial tissue. Staining was seen in the pachytene, but not around the rim of the tubules and not in the center of the tubules where the most mature sperm were located. The signal is most intense in pachytene just before the round spermatids are formed, stages 8–14, and decreased as the sperm matured. The signal followed the residual body when it is pinched off from the mature sperm.

Example 9

Stage Specific Northern Analysis

Stage synchronized testes were obtained from adult Sprague-Dawley rats as described by Wright et al. (*Biology of Reproduction* 29:257–70, 1983). Seminiferous tubule fragments corresponding to the following stages I, II-III, IV-V, VI, VIIab, VIIcd, VIII, IX-XI, XII, XIII-XIV, in the cycle of the seminiferous epithelium were used. The isolated tubule fragments were solublized in TriZol (Life Technologies) and total RNA was isolated according to manufacturer's instructions. The total RNA was quantitated and 7.5 μg of total RNA from each stage was fractionated using a 1.2% agarose gel in 1% formaldehyde and MOPS buffer, transferred to nylon membrane, and cross-linked. The blots were probed with $^{32}$P labeled, full length zins2 DNA (Eco RI-Xho I digest). The probe was heat denatured and added to pre-hybridization solution for overnight hybridization. Blots were washed at room temperature, 2×SSC/0.1% SDS for 10 minutes, the 65° C. 0.2% SSC/0.1% SDS, twice for 15 minutes. Blots were then exposed to film. As a loading control, the blot was probed with $^{32}$P-labeled cyclophilin.

The results of the Northern Blot analysis indicate that the zins2 gene is regulated during the cycle of the seminiferous epithelium. Table 5 shows the amount of the zins2 gene relative to cyclophilin at the various stages tested.

TABLE 5

| Fragment | Zins2/Cyclophilin |
|---|---|
| I | 0.496 |
| II–III | 0.681 |
| IV–V | 0.820 |

TABLE 5-continued

| Fragment | Zins2/Cyclophilin |
|---|---|
| VI | 0.558 |
| VIIab | 0.392 |
| VIIcd | 0.301 |
| VIII | 0.335 |
| IX–XI | 0.300 |
| XII | 0.319 |
| XIII–XIV | 0.549 |

The gene encoding zins2 rises between XII, XIII-XIV and continues to rise until stage IV-V, after which time it decreases steadily and reaches a basal level at stage VIIcd, where it remains until it increases again between stages IX-XI and XII.

A second set of blots were prepared as described above and probed with the gene encoding the rat prohormone convertase PC4 (Seidah et al., *Mol. Endo.* 6:1556–70, 1992). Rat testis cDNA was derived from Sprague Dawley rats (90 days old) by reverse transcription reaction. The rat PC4 probe was generated using polymerase chain reactions as follows: 1.0 μl of adult rat testis cDNA, 1.5 mM Mgcl$_2$ (Life Technologies), 100 μM dNTPs (Life Technologies), 1×PCR Buffer (Life Technologies), 1 μM each of the 5' (SEQ ID NO:14) and 3' (SEQ ID NO:15) oligo nucleotide primers, 2.5 units TAQ polymerase (Life Technologies) and dH$_2$O to a final volume of 50 μl. The reactions were exposed to 30 cycles of: 95° C. denaturation for 30 seconds, 55° C. annealing for 30 seconds, 72° C. extension for 1 minute, followed by a final 10 minute extension at 72° C. The probe was purified using a QIAQUICK PCR purification kit (Qiagen) according to the manufacturer's instructions and the sequence of the probe was verified by sequence analysis. The probe was 32P labeled and the blots were probed as described above.

The Northern Blot analysis indicated two bands corresponding to PC4 in most samples, one at 2.8 kD and one at 1.9 kD. Table 6 shows the amount of the rat PC4 gene relative to CHO B at the various stages tested.

TABLE 6

| | PC4/CHO B | | |
|---|---|---|---|
| Stage | 2.8 kD | 1.9 kD | Total |
| I | 0.447 | 0.153 | 0.600 |
| II–III | 0.685 | 0.115 | 0.800 |
| IV–V | 0.814 | 0.069 | 0.840 |
| VI | 0.900 | 0.100 | 1.00 |
| VIIab | 0.748 | 0.184 | 0.932 |
| VIIcd | 0.598 | 0.251 | 0.850 |
| VIII | 0.570 | 0.279 | 0.850 |
| IX–XI | 0.520 | 0.245 | 0.765 |
| XII | 0.504 | 0.235 | 0.738 |
| XIII–XIV | 0.483 | 0.172 | 0.655 |

The expression pattern of the 2.8 kD band is similar to that of zins2. The expression pattern of the 1.9 kD band runs opposite of the 2.8 kD band, it is low then the 2.8 kD band is highest and increases occur as the 2.8 kD band is decreasing.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. An antibody, or antibody fragment, that specifically binds to a Zins2 testis-specific insulin homolog polypeptide, wherein the Zins2 polypeptide has an amino acid sequence comprising SEQ ID NO:13.

2. The antibody, or antibody fragment, of claim 1, wherein the antibody, or antibody fragment, is selected from the group consisting of: (a) a polyclonal antibody, (b) a murine monoclonal antibody, (c) a humanized antibody derived from (b), (d) a chimeric antibody, (e) a neutralizing antibody, (f) a single chain antibody, and (g) a human monoclonal antibody.

3. The antibody fragment of claim 1, wherein the antibody fragment is selected from the group consisting of: (a) an F(ab')$_2$ fragment, (b) an Fab proteolytic fragment, and (c) an Fv fragment.

4. The antibody, or antibody fragment of claim 1, wherein the antibody or antibody fragment, further comprises a radionuclide, enzyme, substrate, cofactor, fluorescent marker, chemiluminescent marker, peptide tag, magnetic particle, drug, or toxin.

5. An antibody, or antibody fragment, wherein the antibody, or antibody fragment, specifically binds to an epitope of a Zins2 testis-specific insulin homolog polypeptide, wherein the Zins2 polypeptide has an amino acid sequence comprising SEQ ID NO:13.

6. The antibody of claim 5, wherein the antibody is selected from the group consisting of: (a) a polyclonal antibody, (b) a murine monoclonal antibody, (c) a humanized antibody derived from (b), (d) a chimeric antibody, (e) a neutralizing antibody, (f) a single chain antibody, and (g) a human monoclonal antibody.

7. The antibody fragment of claim 5, wherein the antibody fragment is selected from the group consisting of: (a) an F(ab')$_2$ fragment, (b) an Fab proteolytic fragment, and (c) an Fv fragment.

8. The antibody of claim 5, wherein the antibody or antibody fragment, further comprises a radionuclide, enzyme, substrate, cofactor, fluorescent marker, chemiluminescent marker, peptide tag, magnetic particle, drug, or toxin.

9. An antibody comprising a monoclonal antibody that specifically binds to SEQ ID NO:13.

10. The antibody of claim 9, wherein the antibody further comprises a radionuclide, enzyme, substrate, cofactor, fluorescent marker, chemiluminescent marker, peptide tag, magnetic particle, drug, or toxin.

11. The antibody of claim 9, wherein the antibody is selected from the group consisting of: (a) a murine monoclonal antibody, (b) a humanized antibody derived from (a), (c) an antibody fragment, (d) a human monoclonal antibody, (e) a chimeric antibody, (f) a neutralizing antibody, and (g) a single chain antibody.

12. An antibody, or antibody fragment, wherein the antibody, or antibody fragment, specifically binds to an epitope of a Zins2 testis-specific insulin homolog polypeptide, wherein the Zins2 polypeptide has an amino acid sequence consisting of SEQ ID NO:13.

13. The antibody, or antibody fragment of claim 12, wherein the antibody, or antibody fragment, is selected from the group consisting of: (a) a polyclonal antibody, (b) a murine monoclonal antibody, (c) a humanized antibody derived from (b), (d) a chimeric antibody, (e) a neutralizing antibody, (f) a single chain antibody, and (g) a human monoclonal antibody.

14. The antibody fragment of claim 12, wherein the antibody fragment is selected from the group consisting of: (a) an F(ab')$_2$ fragment, (b) an Fab proteolytic fragment, and (c) an Fv fragment.

15. The antibody, or antibody fragment of claim 12, wherein the antibody or antibody fragment, further comprises a radionuclide, enzyme, substrate, cofactor, fluorescent marker, chemiluminescent marker, peptide tag, magnetic particle, drug, or toxin.

16. The antibody, or antibody fragment of claim 5, wherein the epitope is selected from the group consisting of:

(a) an epitope consisting of the amino acid sequence of SEQ ID NO:13 from amino acid number 20 (Ser) to amino acid number 54 (Arg), (b) an epitope consisting of the amino acid sequence of SEQ ID NO:13 from amino acid number 21 (Arg) to amino acid number 53 (Phe), (c) an epitope consisting of the amino acid sequence of SEQ ID NO:13 from amino acid number 23 (Leu) to amino acid number 53 (Phe), (d) an epitope consisting of the amino acid sequence of SEQ ID NO:13 from amino acid number 23 (Leu) to amino acid number 54 (Arg), (e) an epitope consisting of the amino acid sequence of SEQ ID NO:13 from amino acid number 35 (Arg) to amino acid number 41 (Ile), (f) an epitope consisting of the amino acid sequence of SEQ ID NO:13 from amino acid number 172 (Arg) to amino acid number 213 (Tyr), (g) an epitope consisting of the amino acid sequence of SEQ ID NO:13 from amino acid number 173 (Gly) to amino acid number 198 (Phe), (h) an epitope consisting of the amino acid sequence of SEQ ID NO:13 from amino acid number 173 (Gly) to amino acid number 199 (Lys), (i) an epitope consisting of the amino acid sequence of SEQ ID NO:13 from amino acid number 173 (Gly) to amino acid number 200 (Arg), (j) an epitope consisting of the amino acid sequence of SEQ ID NO:13 from amino acid number 55 (Phe) to amino acid number 172 (Arg), and (k) an epitope consisting of the amino acid sequence of SEQ ID NO:13 from amino acid number 201 (Leu) to amino acid number 213 (Tyr).

17. A method of producing an antibody to a polypeptide comprising:

(i) inoculating an animal with a polypeptide selected from the group consisting of:

(a) a polypeptide consisting of the amino acid sequence of SEQ ID NO:13 from amino acid number 20 (Ser) to amino acid number 54 (Arg), (b) a polypeptide consisting of the amino acid sequence of SEQ ID NO:13 from amino acid number 21 (Arg) to amino acid number 53 (Phe), (c) a polypeptide consisting of the amino acid sequence of SEQ ID NO:13 from amino acid number 23 (Leu) to amino acid number 53 (Phe), (d) a polypeptide consisting of the amino acid sequence of SEQ ID NO:13 from amino acid number 23 (Leu) to amino acid number 54 (Arg), (e) an epitope consisting of the amino acid sequence of SEQ ID NO:13 from amino acid number 35 (Arg) to amino acid number 41 (Ile), (f) a polypeptide consisting of the amino acid sequence of SEQ ID NO:13 from amino acid number 172 (Arg) to amino acid number 213 (Tyr), (g) a polypeptide consisting of the amino acid sequence of SEQ ID NO:13 from amino acid number 173 (Gly) to amino acid number 198 (Phe), (h) a polypeptide consisting of the amino acid sequence of SEQ ID NO:13 from amino acid number 173 (Gly) to amino acid number 199 (Lys), (i) a polypeptide consisting of the amino acid sequence of SEQ ID NO:13 from amino acid number 173 (Gly) to amino acid number 200 (Arg), (j) a polypeptide consisting of the amino acid sequence of SEQ ID NO:13 from amino acid number 55 (Phe) to amino acid number 172 (Arg), (k) a polypeptide consisting of the amino acid sequence of SEQ ID NO:13 from amino acid number 201 (Leu) to amino acid number 213 (Tyr), and (l) a polypeptide consisting of the amino acid sequence of SEQ ID NO:13, wherein the polypeptide elicits an immune response in the animal to produce the antibody; and (ii) isolating the antibody from the animal, wherein the antibody specifically binds to a Zins2 testis-specific insulin homolog (SEQ ID NO:13).

18. The antibody of claim 17, wherein the antibody is selected from the group consisting of: (a) a polyclonal antibody, (b) a murine monoclonal antibody, (c) a humanized antibody derived from (b), (d) a chimeric antibody, (e) a neutralizing antibody, (f) a single chain antibody, and (g) a human monoclonal antibody.

19. The antibody of claim 17, wherein the antibody further comprises a radionuclide, enzyme, substrate, cofactor, fluorescent marker, chemiluminescent marker, peptide tag, magnetic particle, drug, or toxin.

\* \* \* \* \*

SEQUENCE LISTING

<160> NUMBER OF SEQ ID NOS: 24

<210> SEQ ID NO 1
<211> LENGTH: 566
<212> TYPE: DNA
<213> ORGANISM: Rattus norvegicus
<220> FEATURE:
<221> NAME/KEY: CDS
<222> LOCATION: (1)...(566)

<400> SEQUENCE: 1

| | | | | | | | | | | | | | | | | |
|---|---|---|---|---|---|---|---|---|---|---|---|---|---|---|---|---|
| atg | aag | cag | ctg | tgc | tgt | tct | tgt | ctg | ttg | tgg | ctt | gga | ctc | cta | ctg | 48 |
| Met | Lys | Gln | Leu | Cys | Cys | Ser | Cys | Leu | Leu | Trp | Leu | Gly | Leu | Leu | Leu | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| gct | cct | ttc | tcc | cag | gaa | caa | gaa | gag | gtc | acc | agc | ccc | acg | aag | ttg | 96 |
| Ala | Pro | Phe | Ser | Gln | Glu | Gln | Glu | Glu | Val | Thr | Ser | Pro | Thr | Lys | Leu | |
| | | | 20 | | | | | 25 | | | | | 30 | | | |

| | | | | | | | | | | | | | | | | |
|---|---|---|---|---|---|---|---|---|---|---|---|---|---|---|---|---|
| tgc | ggc | agg | gac | ctg | ttg | gta | gaa | gtt | ata | aaa | ctc | tgt | ggc | caa | aat | 144 |
| Cys | Gly | Arg | Asp | Leu | Leu | Val | Glu | Val | Ile | Lys | Leu | Cys | Gly | Gln | Asn | |
| | | 35 | | | | | 40 | | | | | 45 | | | | |

| | | | | | | | | | | | | | | | | |
|---|---|---|---|---|---|---|---|---|---|---|---|---|---|---|---|---|
| gac | tgg | agc | cgg | ttc | tcg | atg | gaa | gag | caa | agt | cct | atg | aca | gag | ttg | 192 |
| Asp | Trp | Ser | Arg | Phe | Ser | Met | Glu | Glu | Gln | Ser | Pro | Met | Thr | Glu | Leu | |
| | 50 | | | | | 55 | | | | | 60 | | | | | |

| | | | | | | | | | | | | | | | | |
|---|---|---|---|---|---|---|---|---|---|---|---|---|---|---|---|---|
| gtt | ccc | caa | tat | aca | cgg | aaa | gtc | aaa | acc | ttc | aac | cct | cac | cgg | tcc | 240 |
| Val | Pro | Gln | Tyr | Thr | Arg | Lys | Val | Lys | Thr | Phe | Asn | Pro | His | Arg | Ser | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| tcc | tcc | tcc | tgg | gga | aga | ttc | aca | aac | cca | ggc | gtc | tcc | cag | aag | aaa | 288 |
| Ser | Ser | Ser | Trp | Gly | Arg | Phe | Thr | Asn | Pro | Gly | Val | Ser | Gln | Lys | Lys | |
| | | | | 85 | | | | | 90 | | | | | 95 | | |

| | | | | | | | | | | | | | | | | |
|---|---|---|---|---|---|---|---|---|---|---|---|---|---|---|---|---|
| gca | aca | cac | act | tgg | gaa | tct | cag | tca | ctg | ccc | aac | tat | cag | ctt | aaa | 336 |
| Ala | Thr | His | Thr | Trp | Glu | Ser | Gln | Ser | Leu | Pro | Asn | Tyr | Gln | Leu | Lys | |
| | | | 100 | | | | | 105 | | | | | 110 | | | |

| | | | | | | | | | | | | | | | | |
|---|---|---|---|---|---|---|---|---|---|---|---|---|---|---|---|---|
| aag | gag | gag | ctg | ctt | ccg | aag | aca | gga | gtg | cat | tca | tac | cac | ggt | ggc | 384 |
| Lys | Glu | Glu | Leu | Leu | Pro | Lys | Thr | Gly | Val | His | Ser | Tyr | His | Gly | Gly | |
| | | 115 | | | | | 120 | | | | | 125 | | | | |

| | | | | | | | | | | | | | | | | |
|---|---|---|---|---|---|---|---|---|---|---|---|---|---|---|---|---|
| aag | ccc | tat | gtg | aag | agt | gta | aaa | ttt | cag | aag | aaa | aac | act | gac | aaa | 432 |
| Lys | Pro | Tyr | Val | Lys | Ser | Val | Lys | Phe | Gln | Lys | Lys | Asn | Thr | Asp | Lys | |
| | 130 | | | | | 135 | | | | | 140 | | | | | |

| | | | | | | | | | | | | | | | | |
|---|---|---|---|---|---|---|---|---|---|---|---|---|---|---|---|---|
| atg | agt | acc | ttc | agc | ggc | tta | ttt | tgg | ggg | aac | cat | ccc | cag | agg | aag | 480 |
| Met | Ser | Thr | Phe | Ser | Gly | Leu | Phe | Trp | Gly | Asn | His | Pro | Gln | Arg | Lys | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| cgc | aga | ggt | ttc | gca | gat | aaa | tgc | tgt | gct | ata | ggg | tgc | tcc | aaa | gag | 528 |
| Arg | Arg | Gly | Phe | Ala | Asp | Lys | Cys | Cys | Ala | Ile | Gly | Cys | Ser | Lys | Glu | |
| | | | | 165 | | | | | 170 | | | | | 175 | | |

| | | | | | | | | | | | | |
|---|---|---|---|---|---|---|---|---|---|---|---|---|
| gag | ctg | gcc | gtc | gca | tgc | ctt | ccg | ttt | gtt | gat | ttt | ta | 566 |
| Glu | Leu | Ala | Val | Ala | Cys | Leu | Pro | Phe | Val | Asp | Phe | | |
| | | | 180 | | | | | 185 | | | | | |

<210> SEQ ID NO 2
<211> LENGTH: 188
<212> TYPE: PRT
<213> ORGANISM: Rattus norvegicus

<400> SEQUENCE: 2

| | | | | | | | | | | | | | | | |
|---|---|---|---|---|---|---|---|---|---|---|---|---|---|---|---|
| Met | Lys | Gln | Leu | Cys | Cys | Ser | Cys | Leu | Leu | Trp | Leu | Gly | Leu | Leu | Leu |
| 1 | | | | 5 | | | | | 10 | | | | | 15 | |

| | | | | | | | | | | | | | | | |
|---|---|---|---|---|---|---|---|---|---|---|---|---|---|---|---|
| Ala | Pro | Phe | Ser | Gln | Glu | Gln | Glu | Glu | Val | Thr | Ser | Pro | Thr | Lys | Leu |
| | | | 20 | | | | | 25 | | | | | 30 | | |

| | | | | | | | | | | | | | | | |
|---|---|---|---|---|---|---|---|---|---|---|---|---|---|---|---|
| Cys | Gly | Arg | Asp | Leu | Leu | Val | Glu | Val | Ile | Lys | Leu | Cys | Gly | Gln | Asn |
| | | 35 | | | | | 40 | | | | | 45 | | | |

```
Asp Trp Ser Arg Phe Ser Met Glu Glu Gln Ser Pro Met Thr Glu Leu
     50                  55                  60
Val Pro Gln Tyr Thr Arg Lys Val Lys Thr Phe Asn Pro His Arg Ser
 65                  70                  75                  80
Ser Ser Ser Trp Gly Arg Phe Thr Asn Pro Gly Val Ser Gln Lys Lys
                 85                  90                  95
Ala Thr His Thr Trp Glu Ser Gln Ser Leu Pro Asn Tyr Gln Leu Lys
                100                 105                 110
Lys Glu Glu Leu Leu Pro Lys Thr Gly Val His Ser Tyr His Gly Gly
                115                 120                 125
Lys Pro Tyr Val Lys Ser Val Lys Phe Gln Lys Lys Asn Thr Asp Lys
            130                 135                 140
Met Ser Thr Phe Ser Gly Leu Phe Trp Gly Asn His Pro Gln Arg Lys
145                 150                 155                 160
Arg Arg Gly Phe Ala Asp Lys Cys Cys Ala Ile Gly Cys Ser Lys Glu
                165                 170                 175
Glu Leu Ala Val Ala Cys Leu Pro Phe Val Asp Phe
                180                 185
```

<210> SEQ ID NO 3
<211> LENGTH: 49
<212> TYPE: DNA
<213> ORGANISM: Artificial Sequence
<220> FEATURE:
<223> OTHER INFORMATION: Oligonucleotide zc6091

<400> SEQUENCE: 3
gagcacagaa ttcactactc gaggcggccg cttttttttt tttttttt      49

<210> SEQ ID NO 4
<211> LENGTH: 32
<212> TYPE: DNA
<213> ORGANISM: Artificial Sequence
<220> FEATURE:
<223> OTHER INFORMATION: Oligonucleotide ZC10008

<400> SEQUENCE: 4
caggtcgaca ccatgccgcg gctcctccgc tt      32

<210> SEQ ID NO 5
<211> LENGTH: 34
<212> TYPE: DNA
<213> ORGANISM: Artificial Sequence
<220> FEATURE:
<223> OTHER INFORMATION: Oligonucleotide ZC10491

<400> SEQUENCE: 5
gagtctagat tatgtcactc atacaggaaa gctc      34

<210> SEQ ID NO 6
<211> LENGTH: 23
<212> TYPE: DNA
<213> ORGANISM: Artificial Sequence
<220> FEATURE:
<223> OTHER INFORMATION: Oligonucleotide ZC10684

<400> SEQUENCE: 6
tcctccgctt gtccctgctg tgg      23

<210> SEQ ID NO 7
<211> LENGTH: 23

```
<212> TYPE: DNA
<213> ORGANISM: Artificial Sequence
<220> FEATURE:
<223> OTHER INFORMATION: Oligonucleotide ZC10685

<400> SEQUENCE: 7
ctcctcgaaa cggaactggc tcc                                             23

<210> SEQ ID NO 8
<211> LENGTH: 574
<212> TYPE: DNA
<213> ORGANISM: Artificial Sequence
<220> FEATURE:
<223> OTHER INFORMATION: Human testis EST

<400> SEQUENCE: 8
gtcgacacca tgccgcggct cctccgcttg tccctgctgt ggcttggact cctgctggtt      60
cggttttctc gtgaactgag cgacatcagc agtgccagga agctgtgcgg caggtacttg     120
gtgaaagaaa tagaaaaact ctgcggccat gccaactgga gccagttccg tttcgaggag     180
gaaacccctt tctcacggtt gattgcacag gcctcggaga aggtcgaagc ctacagccca     240
taccagttcg aaagcccgca aaccgcttcc ccggcccggg aagaggcac  aaacccagtg     300 tctacttctt gggaagaagc agtaaacagt tgggaaatgc agtcactacc tgagtataag     360
gataaaaagg gatattcacc ccttggtctg ctggagtttg ctggaggccc actccagatg     420
ctgtttgcct gggtatcacc agcagaggct gcagaacagc aaagattgct gcctgttcct     480
tcctctggaa gcttcatccc agaggggcac ccactagatg ccagccagag ctttcctgta     540
tgagtgacat aaggattcaa cttcaacaga attc                                574

<210> SEQ ID NO 9
<211> LENGTH: 26
<212> TYPE: DNA
<213> ORGANISM: Artificial Sequence
<220> FEATURE:
<223> OTHER INFORMATION: Oligonucleotide ZC10491

<400> SEQUENCE: 9
cgaccgccat tgcacaacgc ggagga                                          26

<210> SEQ ID NO 10
<211> LENGTH: 35
<212> TYPE: DNA
<213> ORGANISM: Artificial Sequence
<220> FEATURE:
<223> OTHER INFORMATION: Oligonucleotide ZC10537

<400> SEQUENCE: 10
ataggaggaa aggttgttgt tgacaaagaa acttg                                35

<210> SEQ ID NO 11
<211> LENGTH: 34
<212> TYPE: DNA
<213> ORGANISM: Artificial Sequence
<220> FEATURE:
<223> OTHER INFORMATION: Oligonucleotide ZC10538

<400> SEQUENCE: 11
gacgaattct gttgaagttg aatccttatg tcac                                 34

<210> SEQ ID NO 12
<211> LENGTH: 703
<212> TYPE: DNA
```

<210> ORGANISM: Homo sapiens
<220> FEATURE:
<221> NAME/KEY: CDS
<222> LOCATION: (17)...(658)

<400> SEQUENCE: 12

```
gcctgggtc acaggg atg ccg cgg ctc ctc cgc ttg tcc ctg ctg tgg ctt        52
                 Met Pro Arg Leu Leu Arg Leu Ser Leu Leu Trp Leu
                  1               5                  10 gga ctc ctg ctg gtt cgg ttt tct cgt gaa ctg agc gac atc agc agt        100
Gly Leu Leu Leu Val Arg Phe Ser Arg Glu Leu Ser Asp Ile Ser Ser
         15                  20                  25 gcc agg aag ctg tgc ggc agg tac ttg gtg aaa gaa ata gaa aaa ctc        148
Ala Arg Lys Leu Cys Gly Arg Tyr Leu Val Lys Glu Ile Glu Lys Leu
     30                  35                  40 tgc ggc cat gcc aac tgg agc cag ttc cgt ttc gag gag gaa acc cct        196
Cys Gly His Ala Asn Trp Ser Gln Phe Arg Phe Glu Glu Glu Thr Pro
 45                  50                  55                  60 ttc tca cgg ttg att gca cag gcc tcg gag aag gtc gaa gcc tac agc        244
Phe Ser Arg Leu Ile Ala Gln Ala Ser Glu Lys Val Glu Ala Tyr Ser
                 65                  70                  75 cca tac cag ttc gaa agc ccg caa acc gct tcc ccg gcc cgg gga aga        292
Pro Tyr Gln Phe Glu Ser Pro Gln Thr Ala Ser Pro Ala Arg Gly Arg
             80                  85                  90 ggc aca aac cca gtg tct act tct tgg gaa gaa gca gta aac agt tgg        340
Gly Thr Asn Pro Val Ser Thr Ser Trp Glu Glu Ala Val Asn Ser Trp
         95                 100                 105 gaa atg cag tca cta cct gag tat aag gat aaa aag gga tat tca ccc        388
Glu Met Gln Ser Leu Pro Glu Tyr Lys Asp Lys Lys Gly Tyr Ser Pro
    110                 115                 120 ctt ggt aag aca aga gaa ttt tct tca tca cat aat atc aat gta tat        436
Leu Gly Lys Thr Arg Glu Phe Ser Ser Ser His Asn Ile Asn Val Tyr
125                 130                 135                 140 att cat gag aat gca aaa ttt cag aag aaa cgt aga aac aaa att aaa        484
Ile His Glu Asn Ala Lys Phe Gln Lys Lys Arg Arg Asn Lys Ile Lys
                145                 150                 155 acc tta agc aat ttg ttt tgg ggg cat cat ccc caa aga aaa cgc aga        532
Thr Leu Ser Asn Leu Phe Trp Gly His His Pro Gln Arg Lys Arg Arg
            160                 165                 170 gga tat tca gaa aag tgt tgt ctt aca gga tgt aca aaa gaa gaa ctt        580
Gly Tyr Ser Glu Lys Cys Cys Leu Thr Gly Cys Thr Lys Glu Glu Leu
        175                 180                 185 agc att gca tgt ctt cca tat att gat ttt aaa agg cta aag gaa aaa        628
Ser Ile Ala Cys Leu Pro Tyr Ile Asp Phe Lys Arg Leu Lys Glu Lys
    190                 195                 200 aga tca tca ctt gta act aag ata tac taa ccatcttaga attttttcta        678
Arg Ser Ser Leu Val Thr Lys Ile Tyr *
205                 210 acctaataaa agcttaatac attta                                           703
```

<210> SEQ ID NO 13
<211> LENGTH: 213
<212> TYPE: PRT
<213> ORGANISM: Homo sapiens

<400> SEQUENCE: 13

```
Met Pro Arg Leu Leu Arg Leu Ser Leu Leu Trp Leu Gly Leu Leu Leu
 1               5                  10                  15

Val Arg Phe Ser Arg Glu Leu Ser Asp Ile Ser Ser Ala Arg Lys Leu
            20                  25                  30
```

```
Cys Gly Arg Tyr Leu Val Lys Glu Ile Glu Lys Leu Cys Gly His Ala
            35                  40                  45

Asn Trp Ser Gln Phe Arg Phe Glu Glu Thr Pro Phe Ser Arg Leu
 50                  55                  60

Ile Ala Gln Ala Ser Glu Lys Val Glu Ala Tyr Ser Pro Tyr Gln Phe
 65                  70                  75                  80

Glu Ser Pro Gln Thr Ala Ser Pro Ala Arg Gly Arg Gly Thr Asn Pro
                 85                  90                  95

Val Ser Thr Ser Trp Glu Glu Ala Val Asn Ser Trp Glu Met Gln Ser
            100                 105                 110

Leu Pro Glu Tyr Lys Asp Lys Lys Gly Tyr Ser Pro Leu Gly Lys Thr
            115                 120                 125

Arg Glu Phe Ser Ser Ser His Asn Ile Asn Val Tyr Ile His Glu Asn
            130                 135                 140

Ala Lys Phe Gln Lys Lys Arg Arg Asn Lys Ile Lys Thr Leu Ser Asn
145                 150                 155                 160

Leu Phe Trp Gly His His Pro Gln Arg Lys Arg Gly Tyr Ser Glu
            165                 170                 175

Lys Cys Cys Leu Thr Gly Cys Thr Lys Glu Glu Leu Ser Ile Ala Cys
                180                 185                 190

Leu Pro Tyr Ile Asp Phe Lys Arg Leu Lys Glu Lys Arg Ser Ser Leu
            195                 200                 205

Val Thr Lys Ile Tyr
            210

<210> SEQ ID NO 14
<211> LENGTH: 28
<212> TYPE: DNA
<213> ORGANISM: Artificial Sequence
<220> FEATURE:
<223> OTHER INFORMATION: Rat PC4 5' primer.

<400> SEQUENCE: 14
tggatcccaa gggacaggac agctgtca                                        28

<210> SEQ ID NO 15
<211> LENGTH: 28
<212> TYPE: DNA
<213> ORGANISM: Artificial Sequence
<220> FEATURE:
<223> OTHER INFORMATION: Rat PC4 3' primer.

<400> SEQUENCE: 15
ggaattctgt ggtctgacct cttgtctg                                        28

<210> SEQ ID NO 16
<211> LENGTH: 14
<212> TYPE: PRT
<213> ORGANISM: Artificial Sequence
<220> FEATURE:
<223> OTHER INFORMATION: Motif.
<220> FEATURE:
<221> NAME/KEY: VARIANT
<222> LOCATION: (0)...(0)
<223> OTHER INFORMATION: Xaa is any amino acid residue except cysteine.

<400> SEQUENCE: 16

Leu Cys Gly Xaa Xaa Xaa Xaa Xaa Xaa Xaa Xaa Xaa Cys
 1               5                  10

<210> SEQ ID NO 17
```

-continued

```
<211> LENGTH: 15
<212> TYPE: PRT
<213> ORGANISM: Artificial Sequence
<220> FEATURE:
<223> OTHER INFORMATION: Motif.
<220> FEATURE:
<221> NAME/KEY: VARIANT
<222> LOCATION: (0)...(0)
<223> OTHER INFORMATION: Xaa is any amino acid residue except cysteine.

<400> SEQUENCE: 17

Cys Cys Xaa Xaa Xaa Cys Xaa Xaa Xaa Xaa Xaa Xaa Xaa Xaa Cys
 1               5                  10                  15

<210> SEQ ID NO 18
<211> LENGTH: 127
<212> TYPE: PRT
<213> ORGANISM: Human

<400> SEQUENCE: 18

Met Ser Ser Ser His Leu Phe Tyr Leu Ala Leu Cys Leu Leu Thr Phe
 1               5                  10                  15

Thr Ser Ser Ala Thr Ala Gly Pro Glu Thr Leu Cys Gly Ala Glu Leu
                20                  25                  30

Val Asp Ala Leu Gln Phe Val Cys Gly Asp Arg Gly Phe Tyr Phe Asn
            35                  40                  45

Lys Pro Thr Gly Tyr Gly Ser Ser Arg Arg Ala Pro Gln Thr Gly
    50                  55                  60

Ile Val Asp Glu Cys Cys Phe Arg Ser Cys Asp Leu Arg Arg Leu Glu
65                  70                  75                  80

Met Tyr Cys Ala Pro Leu Lys Pro Ala Lys Ser Ala Arg Ser Val Arg
                85                  90                  95

Ala Gln Arg His Thr Asp Met Pro Lys Thr Gln Lys Glu Val His Leu
            100                 105                 110

Lys Asn Ala Ser Arg Gly Ser Ala Gly Asn Lys Asn Tyr Arg Met
        115                 120                 125

<210> SEQ ID NO 19
<211> LENGTH: 180
<212> TYPE: PRT
<213> ORGANISM: Human

<400> SEQUENCE: 19

Met Gly Ile Pro Met Gly Lys Ser Met Leu Val Leu Leu Thr Phe Leu
 1               5                  10                  15

Ala Phe Ala Ser Cys Cys Ile Ala Ala Tyr Arg Pro Ser Glu Thr Leu
                20                  25                  30

Cys Gly Gly Glu Leu Val Asp Thr Leu Gln Phe Val Cys Gly Asp Arg
            35                  40                  45

Gly Phe Tyr Phe Ser Arg Pro Ala Ser Arg Val Ser Arg Arg Ser Arg
    50                  55                  60

Gly Ile Val Glu Glu Cys Cys Phe Arg Ser Cys Asp Leu Ala Leu Leu
65                  70                  75                  80

Glu Thr Tyr Cys Ala Thr Pro Ala Lys Ser Glu Arg Asp Val Ser Thr
                85                  90                  95

Pro Pro Thr Val Leu Pro Asp Asn Phe Pro Arg Tyr Pro Val Gly Lys
            100                 105                 110

Phe Phe Gln Tyr Asp Thr Trp Lys Gln Ser Thr Gln Arg Leu Arg Arg
        115                 120                 125
```

```
Gly Leu Pro Ala Leu Leu Arg Ala Arg Gly His Val Leu Ala Lys
        130                 135                 140

Glu Leu Glu Ala Phe Arg Glu Ala Lys Arg His Arg Pro Leu Ile Ala
145                 150                 155                 160

Leu Pro Thr Gln Asp Pro Ala His Gly Gly Ala Pro Pro Glu Met Ala
                    165                 170                 175

Ser Asn Arg Lys
            180

<210> SEQ ID NO 20
<211> LENGTH: 110
<212> TYPE: PRT
<213> ORGANISM: Human

<400> SEQUENCE: 20

Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gln His Leu Cys Gly
            20                  25                  30

Ser His Leu Val Glu Ala Leu Tyr Leu Val Cys Gly Glu Arg Gly Phe
        35                  40                  45

Phe Tyr Thr Pro Lys Thr Arg Arg Glu Ala Glu Asp Leu Gln Val Gly
    50                  55                  60

Gln Val Glu Leu Gly Gly Gly Pro Gly Ala Gly Ser Leu Gln Pro Leu
65                  70                  75                  80

Ala Leu Glu Gly Ser Leu Gln Lys Arg Gly Ile Val Glu Gln Cys Cys
                85                  90                  95

Thr Ser Ile Cys Ser Leu Tyr Gln Leu Glu Asn Tyr Cys Asn
            100                 105                 110

<210> SEQ ID NO 21
<211> LENGTH: 185
<212> TYPE: PRT
<213> ORGANISM: Human

<400> SEQUENCE: 21

Met Pro Arg Leu Phe Phe Phe His Leu Leu Gly Val Cys Leu Leu Leu
1               5                   10                  15

Asn Gln Phe Ser Arg Ala Val Ala Asp Ser Trp Met Glu Glu Val Ile
            20                  25                  30

Lys Leu Cys Gly Arg Glu Leu Val Arg Ala Gln Ile Ala Ile Cys Gly
        35                  40                  45

Met Ser Thr Trp Ser Lys Arg Ser Leu Ser Gln Glu Asp Ala Pro Gln
    50                  55                  60

Thr Pro Arg Pro Val Ala Glu Ile Val Pro Ser Phe Ile Asn Lys Asp
65                  70                  75                  80

Thr Glu Thr Ile Asn Met Met Ser Glu Phe Val Ala Asn Leu Pro Gln
                85                  90                  95

Glu Leu Lys Leu Thr Leu Ser Glu Met Gln Pro Ala Leu Pro Gln Leu
            100                 105                 110

Gln Gln His Val Pro Val Leu Lys Asp Ser Ser Leu Leu Phe Glu Glu
        115                 120                 125

Phe Lys Lys Leu Ile Arg Asn Arg Gln Ser Glu Ala Ala Asp Ser Ser
    130                 135                 140

Pro Ser Glu Leu Lys Tyr Leu Gly Leu Asp Thr His Ser Arg Lys Lys
145                 150                 155                 160
```

```
Arg Gln Leu Tyr Ser Ala Leu Ala Asn Lys Cys Cys His Val Gly Cys
                165                 170                 175

Thr Lys Arg Ser Leu Ala Arg Phe Cys
            180                 185

<210> SEQ ID NO 22
<211> LENGTH: 185
<212> TYPE: PRT
<213> ORGANISM: Human

<400> SEQUENCE: 22

Met Pro Arg Leu Phe Leu Phe His Leu Leu Glu Phe Cys Leu Leu Leu
  1               5                  10                  15

Asn Gln Phe Ser Arg Ala Val Ala Ala Lys Trp Lys Asp Asp Val Ile
                 20                  25                  30

Lys Leu Cys Gly Arg Glu Leu Val Arg Ala Gln Ile Ala Ile Cys Gly
             35                  40                  45

Met Ser Thr Trp Ser Lys Arg Ser Leu Ser Gln Glu Asp Ala Pro Gln
 50                  55                  60

Thr Pro Arg Pro Val Ala Glu Ile Val Pro Ser Phe Ile Asn Lys Asp
 65                  70                  75                  80

Thr Glu Thr Ile Ile Ile Met Leu Glu Phe Ile Ala Asn Leu Pro Pro
                 85                  90                  95

Glu Leu Lys Ala Ala Leu Ser Glu Arg Gln Pro Ser Leu Pro Glu Leu
                100                 105                 110

Gln Gln Tyr Val Pro Ala Leu Lys Asp Ser Asn Leu Ser Phe Glu Glu
            115                 120                 125

Phe Lys Lys Leu Ile Arg Asn Arg Gln Ser Glu Ala Ala Asp Ser Asn
130                 135                 140

Pro Ser Glu Leu Lys Tyr Leu Gly Leu Asp Thr His Ser Gln Lys Lys
145                 150                 155                 160

Arg Arg Pro Tyr Val Ala Leu Phe Glu Lys Cys Cys Leu Ile Gly Cys
                165                 170                 175

Thr Lys Arg Ser Leu Ala Lys Tyr Cys
            180                 185

<210> SEQ ID NO 23
<211> LENGTH: 101
<212> TYPE: PRT
<213> ORGANISM: Human

<400> SEQUENCE: 23

Met Asp Pro Arg Leu Pro Ala Trp Ala Leu Val Leu Leu Gly Pro Ala
        1               5                  10                  15
      Leu Val Phe Ala Leu Gly Pro Ala Pro Thr Pro Glu Met Arg Glu Lys
                       20                  25                  30
      Leu Cys Gly His His Phe Val Arg Ala Leu Val Arg Val Cys Gly Gly
                   35                  40                  45
      Pro Arg Trp Ser Thr Glu Ala Arg Arg Pro Ala Ala Gly Gly Asp Leu
       50                  55                  60
      Pro Gln Thr Ser His His Arg His His Arg Ala Ala Ala Thr Asn
       65                  70                  75                  80
      Pro Ala Arg Tyr Cys Cys Leu Ser Gly Cys Thr Gln Gln Asp Leu Leu
                       85                  90                  95
      Thr Leu Cys Pro Tyr
                  100

<210> SEQ ID NO 24
<211> LENGTH: 139
<212> TYPE: PRT
<213> ORGANISM: Human
```

-continued

```
<400> SEQUENCE: 24

Met Ala Ser Leu Phe Arg Ser Tyr Leu Pro Ala Ile Trp Leu Leu Leu
 1               5                  10                 15
Ser Gln Leu Leu Arg Glu Ser Leu Ala Ala Glu Leu Arg Gly Cys Gly
             20                  25                 30
Pro Arg Phe Gly Lys His Leu Leu Ser Tyr Cys Pro Met Pro Glu Lys
         35                  40                 45
Thr Phe Thr Thr Thr Pro Gly Gly Trp Leu Leu Glu Ser Gly Arg Pro
     50                  55                 60
Lys Glu Met Val Ser Thr Ser Asn Asn Lys Asp Gly Gln Ala Leu Gly
 65              70                  75                 80
Thr Thr Ser Glu Phe Ile Pro Asn Leu Ser Pro Glu Leu Lys Lys Pro
                 85                  90                 95
Leu Ser Glu Gly Gln Pro Ser Leu Lys Lys Ile Ile Leu Ser Arg Lys
             100                 105                110
Lys Arg Ser Gly Arg His Arg Phe Asp Pro Phe Cys Cys Glu Val Ile
         115                 120                125
Cys Asp Asp Gly Thr Ser Val Lys Leu Cys Thr
        130                 135
```